US012427247B2

(12) United States Patent
Cowan et al.

(10) Patent No.: US 12,427,247 B2
(45) Date of Patent: Sep. 30, 2025

(54) STOPCOCK APPARATUS FOR ANGIOGRAPHY INJECTOR FLUID PATHS

(71) Applicant: BAYER HEALTHCARE LLC, Whippany, NJ (US)

(72) Inventors: Kevin Cowan, Allison Park, PA (US); James Dedig, Pittsburgh, PA (US); John Haury, Sewickley, PA (US); Patrick Campbell, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 640 days.

(21) Appl. No.: 17/801,975

(22) PCT Filed: Mar. 15, 2021

(86) PCT No.: PCT/US2021/022421
§ 371 (c)(1),
(2) Date: Aug. 24, 2022

(87) PCT Pub. No.: WO2021/188460
PCT Pub. Date: Sep. 23, 2021

(65) Prior Publication Data
US 2023/0139275 A1     May 4, 2023

Related U.S. Application Data

(60) Provisional application No. 62/990,173, filed on Mar. 16, 2020, provisional application No. 62/990,170, (Continued)

(51) Int. Cl.
*A61M 5/145* (2006.01)
*A61M 5/36* (2006.01)
*A61M 39/22* (2006.01)

(52) U.S. Cl.
CPC ........ *A61M 5/14546* (2013.01); *A61M 5/365* (2013.01); *A61M 39/223* (2013.01); *A61M 2039/229* (2013.01)

(58) Field of Classification Search
CPC .............. A61M 5/14546; A61M 5/365; A61M 39/223; A61M 2039/229
See application file for complete search history.

(56) References Cited

U.S. PATENT DOCUMENTS

| 352,715 A | 11/1886 | Sandmark |
|---|---|---|
| 508,584 A | 11/1893 | Stevens |

(Continued)

FOREIGN PATENT DOCUMENTS

| CN | 103917269 A | 7/2014 |
|---|---|---|
| CN | 105521533 A | 4/2016 |

(Continued)

OTHER PUBLICATIONS

Un; Haluk, "A New Device Preventing Air Embolism During the Angiography, Air Trap Device: An In-Vitro Experimental Air Emboli Study", Proceedings of the 2019 Design of Medical Devices Conference, 2019.

(Continued)

*Primary Examiner* — Dung T Ulsh
(74) *Attorney, Agent, or Firm* — Joseph L. Kent; James R. Stevenson

(57) ABSTRACT

A valve assembly for a fluid injector system includes a valve housing, a first port configured for fluid communication with a fluid injector, a second port, a third port, and a fourth port configured for fluid communication with a patient line. The valve assembly includes an air detection region associated with the first port, a fluid path length having a proximal end in fluid communication with the second port and a distal end in fluid communication with the third port, and a valve (Continued)

element defining a first fluid path and a second fluid path. The first fluid path provides fluid communication between the first and second ports in a delivery position of the valve housing. The second fluid path provides fluid communication between the third and fourth ports in the delivery position. The third port is isolated from the fourth port in a stop position of the valve housing.

13 Claims, 20 Drawing Sheets

Related U.S. Application Data filed on Mar. 16, 2020, provisional application No. 62/990,145, filed on Mar. 16, 2020.

(56) References Cited

U.S. PATENT DOCUMENTS

| | | |
|---|---|---|
| 798,093 A | 8/1905 | Edward |
| 817,054 A | 4/1906 | Daniel |
| 937,029 A | 10/1909 | Blessing et al. |
| 945,143 A | 1/1910 | Iacques |
| 1,388,946 A | 8/1921 | Goold |
| 1,930,929 A | 10/1933 | Joel et al. |
| 2,062,285 A | 12/1936 | Sam et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van Sciver, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | James et al. |
| 3,507,278 A | 4/1970 | Winfried |
| 3,527,215 A | 9/1970 | Harry |
| 3,557,788 A | 1/1971 | Betty |
| 3,613,963 A | 10/1971 | Otto |
| 3,618,846 A | 11/1971 | Patrick |
| 3,635,444 A | 1/1972 | Charles |
| 3,671,208 A | 6/1972 | Wayne |
| 3,699,961 A | 10/1972 | Roman |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A | 3/1975 | Harding |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett, III |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,904,239 A | 2/1990 | Winchell et al. |
| 4,952,068 A | 8/1990 | Flint |
| 4,969,879 A | 11/1990 | Lichte |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,399,173 A | 3/1995 | Parks et al. |
| 5,431,185 A | 7/1995 | Shannon et al. |

(56) References Cited

U.S. PATENT DOCUMENTS

| | | |
|---|---|---|
| 5,492,147 A | 2/1996 | Challender et al. |
| 5,507,535 A | 4/1996 | McKamey et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 5,984,378 A | 11/1999 | Ostrander et al. |
| 6,054,194 A | 4/2000 | Kane |
| 6,056,724 A | 5/2000 | Lacroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 * | 1/2001 | Schnell ............... A61M 1/367 604/32 |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans et al. |
| 6,773,417 B2 | 8/2004 | Fitzgibbons et al. |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Hansen |
| 7,011,650 B2 | 3/2006 | Rosoff et al. |
| 7,094,216 B2 | 8/2006 | Trombley, III et al. |
| 7,101,352 B2 | 9/2006 | Dochon et al. |
| 7,192,416 B1 | 3/2007 | Lazzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins et al. |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,666,169 B2 | 2/2010 | Cowan et al. |
| 7,686,788 B2 | 3/2010 | Freyman et al. |
| 7,766,883 B2 | 8/2010 | Rellly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,540,698 B2 | 9/2013 | Spohn et al. |
| 8,740,877 B2 | 6/2014 | Borlaug et al. |
| 8,795,240 B2 | 8/2014 | Chelak |
| 8,872,708 B2 | 10/2014 | Hill et al. |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,945,051 B2 | 2/2015 | Schriver et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 10,933,190 B2 | 3/2021 | Berry et al. |
| 11,083,882 B2 | 8/2021 | Schrauder et al. |
| 11,207,462 B2 | 12/2021 | Cowan et al. |
| 11,389,585 B2 | 7/2022 | Spohn et al. |
| 11,413,403 B2 | 8/2022 | Yoshioka et al. |
| 11,547,793 B2 | 1/2023 | Cowan et al. |
| 2001/0004466 A1 | 6/2001 | Heinz et al. |

(56) References Cited

U.S. PATENT DOCUMENTS

| | | |
|---|---|---|
| 2001/0018575 A1 | 8/2001 | Lyza |
| 2002/0010596 A1 | 1/2002 | Matory |
| 2002/0147429 A1 | 10/2002 | Cowan et al. |
| 2003/0216695 A1 | 11/2003 | Yang |
| 2003/0226539 A1 | 12/2003 | Kim et al. |
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2005/0121103 A1 | 6/2005 | Steigerwalt et al. |
| 2006/0052794 A1 | 3/2006 | McGill et al. |
| 2006/0149213 A1 | 7/2006 | Raybuck |
| 2007/0068964 A1 | 3/2007 | Tanaami et al. |
| 2007/0129705 A1 | 6/2007 | Trombley, III et al. |
| 2008/0045925 A1 | 2/2008 | Stepovich et al. |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0218434 A1 | 9/2011 | Ziemba et al. |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0178629 A1 | 7/2012 | Hudson et al. |
| 2012/0209111 A1 | 8/2012 | Cowan et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1 | 2/2013 | Kirkpatrick |
| 2013/0067416 A1 | 3/2013 | Barron et al. |
| 2013/0204130 A1 | 8/2013 | McArthur et al. |
| 2013/0211248 A1 | 8/2013 | Cowan et al. |
| 2013/0310756 A1 | 11/2013 | Whalley et al. |
| 2014/0124087 A1 | 5/2014 | Anderson et al. |
| 2014/0261713 A1 | 9/2014 | Schriver et al. |
| 2014/0276652 A1 | 9/2014 | Gittard |
| 2014/0374353 A1 | 12/2014 | Wright et al. |
| 2015/0260325 A1 | 9/2015 | Quick |
| 2016/0030662 A1 | 2/2016 | Uber, III et al. |
| 2016/0250409 A1 | 9/2016 | Dedig et al. |
| 2017/0035974 A1 | 2/2017 | Berry et al. |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0161496 A1 | 6/2018 | Berry et al. |
| 2018/0280630 A1 | 10/2018 | Jiang et al. |
| 2018/0296755 A1 | 10/2018 | Dahlin et al. |
| 2019/0240424 A1 | 8/2019 | Yoshioka et al. |
| 2020/0164141 A1 | 5/2020 | Biermann et al. |
| 2020/0206490 A1 | 7/2020 | Bae |
| 2020/0246541 A1 | 8/2020 | Neftel et al. |
| 2021/0023298 A1 | 1/2021 | McDermott |
| 2021/0146064 A1 | 5/2021 | Knutsson |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |
| 2023/0146744 A1 | 5/2023 | Cowan et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 1173662 A | 12/1969 |
| GB | 2214819 A | 9/1989 |
| GB | 2374143 A | 10/2002 |
| JP | H02-88664 | 7/1990 |
| JP | H0849598 A | 2/1996 |
| JP | H10999034 A | 4/1997 |
| JP | 6485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | 2007133942 A2 | 11/2007 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2010014654 A1 | 2/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |
| WO | 2018218132 A1 | 11/2018 |
| WO | 2019046259 A1 | 3/2019 |
| WO | 2019046260 A1 | 3/2019 |
| WO | 2019046299 A1 | 3/2019 |
| WO | 2019152978 A1 | 8/2019 |
| WO | 2019204605 A1 | 10/2019 |
| WO | 2019204617 A1 | 10/2019 |
| WO | 2020055785 A1 | 3/2020 |
| WO | 2020055818 A1 | 3/2020 |

(56) References Cited

FOREIGN PATENT DOCUMENTS

| | | |
|---|---|---|
| WO | 2021050507 A1 | 3/2021 |
| WO | 2021168076 A1 | 8/2021 |
| WO | 2021173743 A1 | 9/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257667 A1 | 12/2021 |
| WO | 2021257699 A1 | 12/2021 |
| WO | 2022035791 A1 | 2/2022 |
| WO | 2022036058 A1 | 2/2022 |
| WO | 2022265695 A1 | 12/2022 |

OTHER PUBLICATIONS

"International Preliminary Report on Patentability from PCT Application No. PCT/US2021/022421", Sep. 29, 2022.

\* cited by examiner

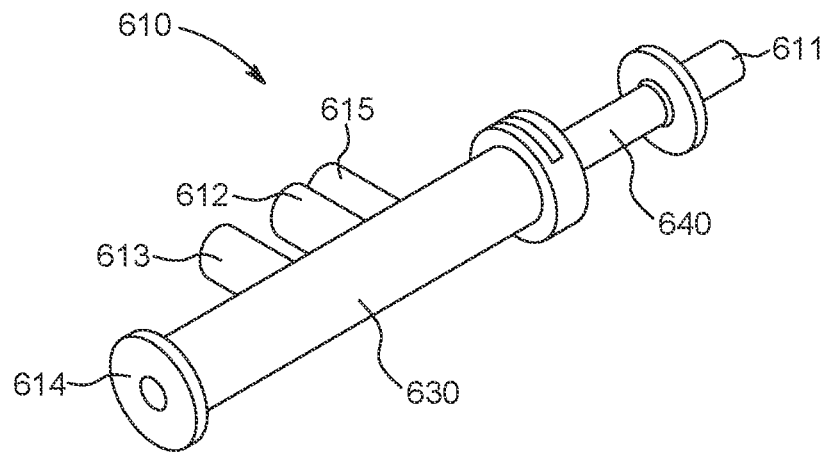
FIG. 24
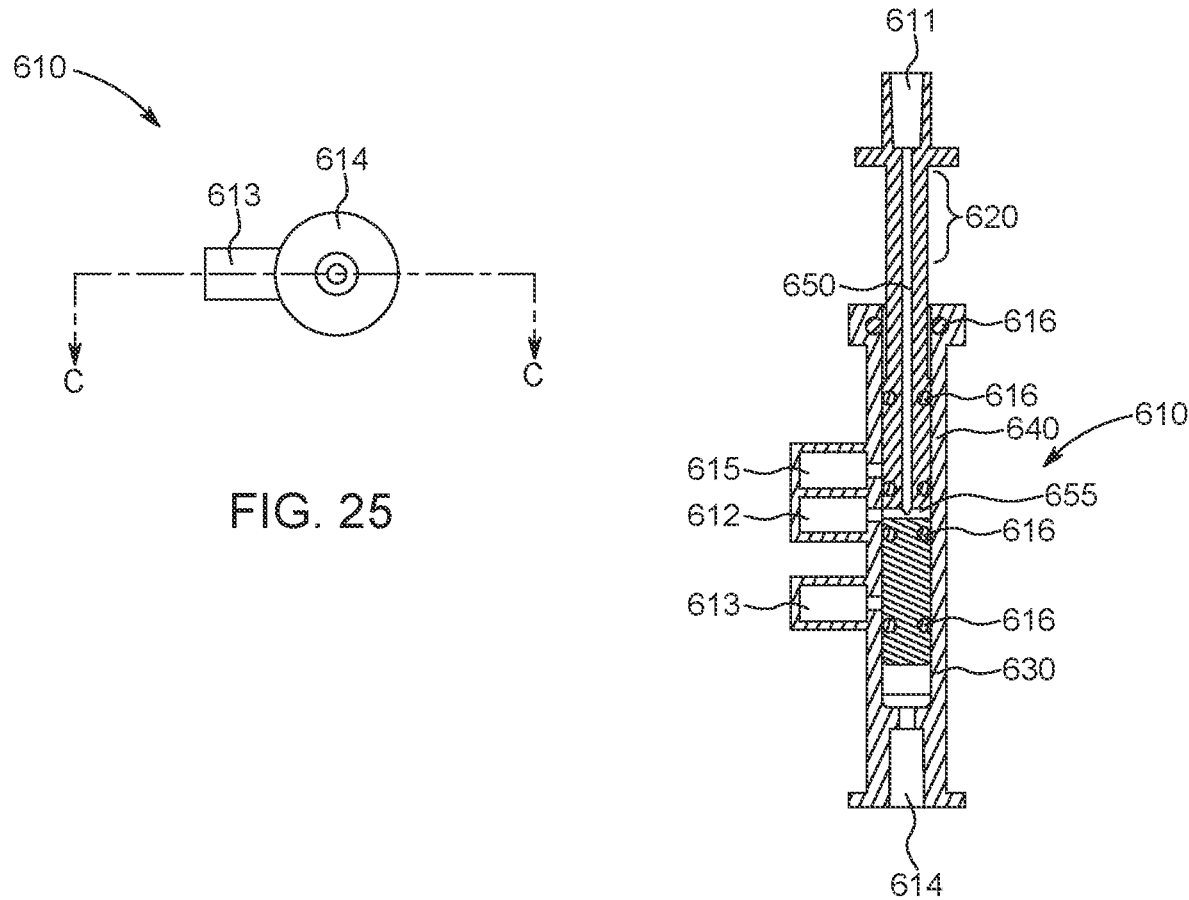
FIG. 25
FIG. 26

STOPCOCK APPARATUS FOR ANGIOGRAPHY INJECTOR FLUID PATHS

CROSS-REFERENCE TO RELATED APPLICATIONS

This application is a U.S. national phase application under 35 U.S.C. § 371 of PCT International Application No. PCT/US2021/022421, filed Mar. 15, 2021, and claims the benefit of U.S. Provisional Patent Application No. 62/990,145, filed on Mar. 16, 2020; U.S. Provisional Patent Application No. 62/990,170 filed on Mar. 16, 2020, and U.S. Provisional Patent Application No. 62/990,173 filed on Mar. 16, 2020, the disclosures of which are hereby incorporated by reference in their entireties.

BACKGROUND OF THE DISCLOSURE

Field of the Disclosure

The present disclosure relates generally to fluid path configurations and apparatuses for use with angiography fluid injectors for high pressure injection of medical fluids. More specifically, the present disclosure describes a fluid delivery system having a valve assembly configured to minimize potential administration of air to a patient during an injection procedure.

Description of Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent (such as saline or Ringer's lactate), and other medical fluids, have been developed for use in procedures such as cardiovascular angiography (CV), computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate.

Typically, fluid injectors have at least one drive member, such as a piston, that connects to the syringe, for example via connection with a plunger or an engagement feature on a proximal end wall of the syringe. The syringe may include a rigid barrel with the syringe plunger being slidably disposed within the barrel. The drive members drive the plungers in a proximal and/or distal direction relative to a longitudinal axis of the barrel to draw fluid into or deliver the fluid from the syringe barrel. In certain applications, such as angiography, the medical fluids are injected directly into the cardiac system at fluid pressures up to 1200 psi.

During certain injection procedures at these high fluid pressures with fluid being administered directly to the cardiac system, it is imperative that no air or other gas bubbles be co-injected with the medical fluid as patient harm may result. Thus, new methods and devices are necessary to detect and prevent inadvertent injection of air during a high-pressure fluid injection procedure. To further complicate matters, at pressures of up to 1200 psi associated with some angiographic procedures, the flow rate of the medical fluid and the compressibility of air compresses any air in the system such that even if air is detected, initiating a shutdown of the injector may not occur fast enough to prevent the air from traversing a considerable distance downstream of the detection point. Furthermore, even if the injection is stopped upon air detection, the air volume may expand rapidly due to release of pressure caused by a system shutdown. In addition, release of system compliance upon cessation of an injection may result in continued fluid flow as the compliance volume is released in the absence of fluid pressure.

SUMMARY OF THE DISCLOSURE

In view of the foregoing, there exists a need for devices, systems, and methods for preventing air from being delivered to a patient during an injection procedure. Embodiments of the present disclosure are directed to a valve assembly for a fluid injector system, the valve assembly includes a valve housing, a first port configured for fluid communication with at least one syringe of a fluid injector, a second port, a third port, and a fourth port configured for fluid communication with a patient line. The valve assembly further includes an air detection region associated with the first port, a fluid path length fluid path length having a proximal end in fluid communication with the second port and a distal end in fluid communication with the third port, and a valve element defining a first valve fluid path and a second valve fluid path. The first valve fluid path provides fluid communication between the first port and the second port when in a delivery position of the valve housing relative to the valve element. The second valve fluid path provides fluid communication between the third port and the fourth port when in the delivery position. The third port is isolated from the fourth port when in a stop position of the valve housing relative to the valve element.

In some embodiments, thee valve assembly, further includes a fifth port configured for fluid communication with a bulk fluid source. The first fluid path provides fluid communication between the first port and the fifth port when in a fill position of the valve housing relative to the valve element.

In some embodiments, the fluid path length includes tubing having a length greater than a distance that an air bubble can travel or expand during an actuation time of the valve assembly. The actuation time of the valve assembly is a time interval between a time at which the air bubble is detected in the air detection region and a time at which the valve assembly reaches the stop position.

In some embodiments, the fluid path length includes tubing have a length of between approximately 1000 millimeters and approximately 1400 millimeters.

In some embodiments, the first port, the second port, the third port, and the fourth port are arranged circumferentially about the valve housing.

In some embodiments, the valve element is rotatable about a longitudinal axis of the valve housing between the delivery position and the stop position.

In some embodiments, the first port is offset relative to the second port along a longitudinal axis of the valve housing.

In some embodiments, the first port is integrally formed with the valve element and in fluid communication with the first valve fluid path.

In some embodiments, the valve housing is slidable relative to the valve element between the delivery position and the stop position.

In some embodiments, at least portions of the first valve fluid path and the second valve fluid path extend parallel to a longitudinal axis of the valve housing.

In some embodiments, fluid path length includes a plurality of longitudinal fluid channels arranged circumferentially about the valve housing, and a plurality of bent fluid channels connecting the plurality of longitudinal fluid channels in series. In some embodiments, the fluid path length includes coiled tubing.

Other embodiments of the present disclosure are directed to a fluid delivery system including at least one powered injector, at least one syringe, at least one air detector, a valve assembly, at least one controller in electrical communication with the at least one air detector. The at least one controller is configured for controlling fluid flow through the valve assembly. The fluid injector system further includes a patient line. The valve assembly includes a valve housing, a first port in fluid communication with the at least one powered injector, a second port, a third port, and a fourth port, a fluid path length having a proximal end in fluid communication with the second port and a distal end in fluid communication with the third port, and a valve element defining a first valve fluid path and a second valve fluid path. The patient line is in fluid communication with the fourth port. The first valve fluid path provides fluid communication between the first port and the second port in a delivery position of the valve housing relative to the valve element. The second valve fluid path provides fluid communication between the third port and the fourth port in the delivery position. The third port is isolated from the fourth port in a stop position of the valve housing relative to the valve element.

In some embodiments, the fluid delivery system further includes an actuator operably associated with the air detector and configured to transition the valve assembly to the stop position upon detection of air bubble by the air detector. The air detector is upstream of or within the first port and configured to detect an air bubble flowing out of the at least one syringe.

In some embodiments, the fluid path length includes tubing having a length greater than a distance that the air bubble can travel or expand during an actuation time of the valve assembly. The actuation time of the valve assembly is a time interval between a time at which the air bubble is detected by the air detector and a time at which the valve assembly reaches the stop position.

In some embodiments, the fluid delivery system further includes a bulk fluid source, the valve assembly further includes a fifth port in fluid communication with the bulk fluid source, and the first valve fluid path provides fluid communication between the first port and the fifth port when in a fill position of the valve housing relative to the valve element.

In some embodiments, the fluid path length includes tubing having a length greater than a distance that an air bubble can travel or expand during an actuation time of the valve assembly. The actuation time of the valve assembly is a time interval between a time at which the air bubble is detected in the air detection region and a time at which the valve assembly reaches the stop position.

In some embodiments, the fluid path length includes tubing have a length of between approximately 1000 millimeters and approximately 1400 millimeters.

In some embodiments, the first port, the second port, the third port, and the fourth port are arranged circumferentially about the valve housing In some embodiments, the valve element is rotatable about a longitudinal axis of the valve housing between the delivery position and the stop position.

In some embodiments, the first port is offset relative to the second port along a longitudinal axis of the valve housing.

In some embodiments, the first port is integrally formed with the valve element and in fluid communication with the first valve fluid path.

In some embodiments, the valve housing is slidable relative to the valve element between the delivery position and the stop position.

In some embodiments, at least portions of the first valve fluid path and the second valve fluid path extend parallel to a longitudinal axis of the valve housing.

In some embodiments, the fluid path length includes a plurality of longitudinal fluid channels arranged circumferentially about the valve housing, and a plurality of bent fluid channels connecting the plurality of longitudinal fluid channels in series.

In some embodiments, the fluid path length includes coiled tubing.

Other embodiment of the present disclosure are directed to a method of trapping an air bubble in a fluid path length during an injection procedure performed by a fluid delivery system. The method includes detecting an air bubble flowing distally from at least one syringe and into a valve assembly with at least one air detector, the valve assembly including a including a first port, a second port, a third port, and a fourth port. The method further includes actuating the valve assembly to isolate the third port from the fourth port, thereby trapping the air bubble in the fluid path length between the second port and the third port. Actuating the valve assembly occurs within 60 and 100 milliseconds after detecting the air bubble with the air detector.

In some embodiments, the fluid path length includes tubing having a length greater than a distance that the air bubble can travel or expand during an actuation time of the valve assembly. The actuation time of the valve assembly is a time interval between a time at which the air bubble is detected and a time at which the third port is isolated from the fourth port.

In some embodiments, actuating the valve assembly includes rotating a valve element of the valve assembly relative to a valve housing of the valve assembly.

In some embodiments, actuating the valve assembly includes sliding the valve housing of the valve assembly relative to the valve element of the valve assembly.

In some embodiments, the fluid path length includes tubing have a length of between approximately 1000 millimeters and approximately 1400 millimeters.

In some embodiments, the valve assembly includes a valve housing. The first port, the second port, the third port, and the fourth port are arranged circumferentially about the valve housing.

In some embodiments, the valve assembly includes a valve element rotatable about a longitudinal axis of the valve housing between the delivery position and the stop position.

In some embodiments, the first port is offset relative to the second port along a longitudinal axis of the valve housing.

In some embodiments, the first port is integrally formed with the valve element.

In some embodiments, the valve housing is slidable relative to the valve element between the delivery position and the stop position.

In some embodiments, the valve element includes a first valve fluid path and a second valve fluid path. At least portions of the first fluid path and the second fluid path extend parallel to a longitudinal axis of the valve housing.

In some embodiments, the fluid path length includes a plurality of longitudinal fluid channels arranged circumferentially about the valve housing, and a plurality of bent fluid channels connecting the plurality of longitudinal fluid channels in series. In some embodiments, the fluid path length includes coiled tubing.

Further aspects or examples of the present disclosure are described in the following numbered clauses:

Clause 1. A valve assembly for a fluid injector system, the valve assembly comprising: a valve housing; a first port configured for fluid communication with at least one syringe of a fluid injector, a second port, a third port, and a fourth port configured for fluid communication with a patient line; an air detection region associated with the first port; a fluid path length having a proximal end in fluid communication with the second port and a distal end in fluid communication with the third port; and a valve element defining a first valve fluid path and a second valve fluid path, wherein the first valve fluid path provides fluid communication between the first port and the second port when in a delivery position of the valve housing relative to the valve element, wherein the second valve fluid path provides fluid communication between the third port and the fourth port when in the delivery position, and wherein the third port is isolated from the fourth port when in a stop position of the valve housing relative to the valve element.

Clause 2. The valve assembly of clause 1, further comprising a fifth port configured for fluid communication with a bulk fluid source, wherein the first fluid path provides fluid communication between the first port and the fifth port when in a fill position of the valve housing relative to the valve element.

Clause 3. The valve assembly of clause 1 or 2, wherein the fluid path length comprises tubing having a length greater than a distance that an air bubble can travel or expand during an actuation time of the valve assembly, wherein the actuation time of the valve assembly is a time interval between a time at which the air bubble is detected in the air detection region and a time at which the valve assembly reaches the stop position.

Clause 4. The valve assembly of any of clauses 1 to 3, wherein the fluid path length comprises tubing have a length of between approximately 1000 millimeters and approximately 1400 millimeters.

Clause 5. The valve assembly of any of clauses 1 to 4, wherein the first port, the second port, the third port, and the fourth port are arranged circumferentially about the valve housing.

Clause 6. The valve assembly of any of clauses 1 to 5, wherein the valve element is rotatable about a longitudinal axis of the valve housing between the delivery position and the stop position.

Clause 7. The valve assembly of any of clauses 1 to 6, wherein the first port is offset relative to the second port along a longitudinal axis of the valve housing.

Clause 8. The valve assembly of any of clauses 1 to 7, where the first port is integrally formed with the valve element and in fluid communication with the first valve fluid path.

Clause 9. The valve assembly of any of clauses 1 to 8, wherein the valve housing is slidable relative to the valve element between the delivery position and the stop position.

Clause 10. The valve assembly of any of clauses 1 to 9, wherein at least portions of the first valve fluid path and the second valve fluid path extend parallel to a longitudinal axis of the valve housing.

Clause 11. The valve assembly of any of clauses 1 to 10, wherein the fluid path length comprises: a plurality of longitudinal fluid channels arranged circumferentially about the valve housing; and a plurality of bent fluid channels connecting the plurality of longitudinal fluid channels in series.

Clause 12. The valve assembly of any of clauses 1 to 11, wherein the fluid path length comprises coiled tubing.

Clause 13. A fluid delivery system comprising: at least one powered injector; at least one syringe; at least one air detector; a valve assembly; at least one controller in electrical communication with the at least one air detector, wherein the at least one controller is configured for controlling fluid flow through the valve assembly; and a patient line, wherein the valve assembly comprises: a valve housing; a first port in fluid communication with the at least one powered injector, a second port, a third port, and a fourth port; a fluid path length having a proximal end in fluid communication with the second port and a distal end in fluid communication with the third port; and a valve element defining a first valve fluid path and a second valve fluid path; and wherein the patient line is in fluid communication with the fourth port, wherein the first valve fluid path provides fluid communication between the first port and the second port in a delivery position of the valve housing relative to the valve element, wherein the second valve fluid path provides fluid communication between the third port and the fourth port in the delivery position, and wherein the third port is isolated from the fourth port in a stop position of the valve housing relative to the valve element.

Clause 14. The fluid delivery system of clause 13, further comprising: an actuator operably associated with the air detector and configured to transition the valve assembly to the stop position upon detection of air bubble by the air detector, wherein the air detector is upstream of or within the first port and configured to detect an air bubble flowing out of the at least one syringe.

Clause 15. The fluid delivery system of clause 13 or 14, wherein the fluid path length comprises tubing having a length greater than a distance that the air bubble can travel or expand during an actuation time of the valve assembly, wherein the actuation time of the valve assembly is a time interval between a time at which the air bubble is detected by the air detector and a time at which the valve assembly reaches the stop position.

Clause 16. The fluid delivery system of any of clauses 13 to 15, further comprising a bulk fluid source, wherein the valve assembly further comprises a fifth port in fluid communication with the bulk fluid source, and wherein the first valve fluid path provides fluid communication between the first port and the fifth port when in a fill position of the valve housing relative to the valve element.

Clause 17. The fluid delivery system of any of clauses 13 to 16, wherein the fluid path length comprises tubing having a length greater than a distance that an air bubble can travel or expand during an actuation time of the valve assembly, wherein the actuation time of the valve assembly is a time interval between a time at which the air bubble is detected in the air detection region and a time at which the valve assembly reaches the stop position.

Clause 18. The fluid delivery system of any of clauses 13 to 17, wherein the fluid path length comprises tubing have a length of between approximately 1000 millimeters and approximately 1400 millimeters.

Clause 19. The fluid delivery system of any of clauses 13 to 18, the second port, the third port, and the fourth port are arranged circumferentially about the valve housing Clause 20. The fluid delivery system of any of clauses 13 to 19, wherein the valve element is rotatable about a longitudinal axis of the valve housing between the delivery position and the stop position.

Clause 21. The fluid delivery system of any of clauses 13 to 20, wherein the first port is offset relative to the second port along a longitudinal axis of the valve housing.

Clause 22. The fluid delivery system of any of clauses 13 to 21, where the first port is integrally formed with the valve element and in fluid communication with the first valve fluid path.

Clause 23. The fluid delivery system of any of clauses 13 to 22, wherein the valve housing is slidable relative to the valve element between the delivery position and the stop position.

Clause 24. The fluid delivery system of any of clauses 13 to 23, wherein at least portions of the first valve fluid path and the second valve fluid path extend parallel to a longitudinal axis of the valve housing.

Clause 25. The fluid delivery system of any of clauses 13 to 24, wherein the fluid path length comprises: a plurality of longitudinal fluid channels arranged circumferentially about the valve housing; and a plurality of bent fluid channels connecting the plurality of longitudinal fluid channels in series.

Clause 26. The fluid delivery system of any of clauses 13 to 25, wherein the fluid path length comprises coiled tubing.

Clause 27. A method of trapping an air bubble in a fluid path length during an injection procedure performed by a fluid delivery system, the method comprising: detecting an air bubble flowing distally from at least one syringe and into a valve assembly with at least one air detector, the valve assembly comprising a comprising a first port, a second port, a third port, and a fourth port; and actuating the valve assembly to isolate the third port from the fourth port, thereby trapping the air bubble in the fluid path length between the second port and the third port, wherein actuating the valve assembly occurs within 60 and 100 milliseconds after detecting the air bubble with the air detector.

Clause 28. The method of clause 27, wherein the fluid path length comprises tubing having a length greater than a distance that the air bubble can travel or expand during an actuation time of the valve assembly, wherein the actuation time of the valve assembly is a time interval between a time at which the air bubble is detected and a time at which the third port is isolated from the fourth port.

Clause 29. The method of clause 27 or 28, wherein actuating the valve assembly comprises rotating a valve element of the valve assembly relative to a valve housing of the valve assembly.

Clause 30. The method of any of clauses 27 to 29, wherein actuating the valve assembly comprises sliding the valve housing of the valve assembly relative to the valve element of the valve assembly.

Clause 31. The method of any of clauses 27 to 30, wherein the fluid path length comprises tubing have a length of between approximately 1000 millimeters and approximately 1400 millimeters.

Clause 32. The method of any of clauses 27 to 31, and wherein the first port, the second port, the third port, and the fourth port are arranged circumferentially about the valve housing.

Clause 33. The method of any of clauses 27 to 32, wherein the valve assembly comprises a valve element rotatable about a longitudinal axis of the valve housing between the delivery position and the stop position.

Clause 34. The method of any of clauses 27 to 33, wherein the first port is offset relative to the second port along a longitudinal axis of the valve housing.

Clause 35. The method of any of clauses 27 to 34, where the first port is integrally formed with the valve element.

Clause 36. The method of any of clauses 27 to 35, wherein the valve housing is slidable relative to the valve element between the delivery position and the stop position.

Clause 37. The method of any of clauses 27 to 36, wherein the valve element comprises a first valve fluid path and a second valve fluid path, and wherein at least portions of the first fluid path and the second fluid path extend parallel to a longitudinal axis of the valve housing.

Clause 38. The method of any of clauses 27 to 37, wherein the fluid path length comprises: a plurality of longitudinal fluid channels arranged circumferentially about the valve housing; and a plurality of bent fluid channels connecting the plurality of longitudinal fluid channels in series.

Clause 39. The method of any of clauses 27 to 38, wherein the fluid path length comprises coiled tubing.

Further details and advantages of the various examples described in detail herein will become clear upon reviewing the following detailed description of the various examples in conjunction with the accompanying drawing figures.

BRIEF DESCRIPTION OF THE DRAWINGS

FIG. 24 is a side perspective view of a valve assembly according to an embodiment of the present disclosure;

FIG. 25 is a distal end view of the valve assembly of FIG. 24;

FIG. 26 is a cross-sectional side view of the valve assembly of FIG. 25 along line C-C;

Referring to the drawings in which like reference characters refer to like parts throughout the several views thereof, the present disclosure is generally directed to an in-line air bubble suspension apparatus for use with an angiography injector system.

DETAILED DESCRIPTION

Figure 1:
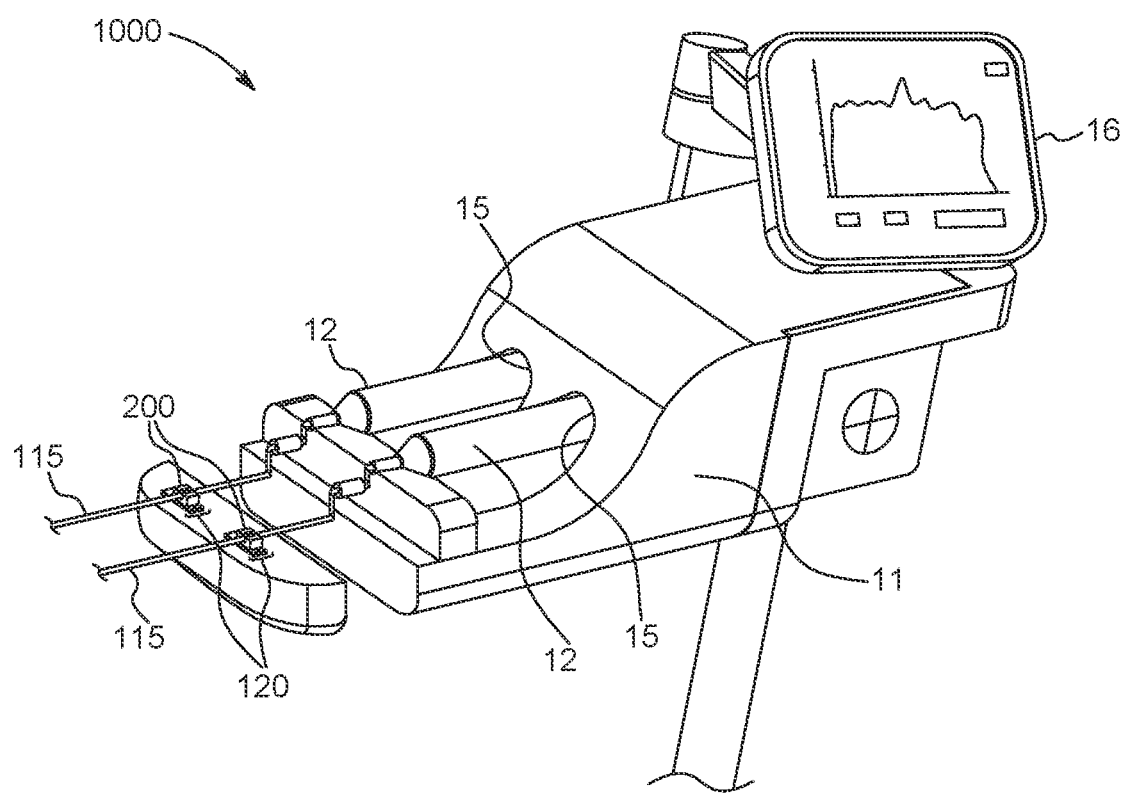
FIG. 1 is a perspective view of a fluid delivery system according to an embodiment of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. Spatial or directional terms, such as "left", "right", "inner", "outer", "above", "below", and the like, are not to be considered as limiting as the invention can assume various alternative orientations.

As used herein, the singular form of "a", "an", and "the" include plural referents unless the context clearly dictates otherwise.

All numbers used in the specification and claims are to be understood as being modified in all instances by the term "about". The terms "approximately", "about", and "substantially" mean a range of plus or minus ten percent of the stated value.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

When used in relation to a component of a fluid delivery system such as a fluid reservoir, a syringe, or a fluid line, the term "distal" refers to a portion of said component nearest to a patient. When used in relation to a component of a fluid injector system such as a fluid reservoir, a syringe, or a fluid line, the term "proximal" refers to a portion of said component nearest to the injector of the fluid injector system (i.e. the portion of said component farthest from the patient). When used in relation to a component of a fluid delivery system such as a fluid reservoir, a syringe, or a fluid line, the term "upstream" refers to a direction away from the patient and towards the injector of the fluid injector system. For example, if a first component is referred to as being "upstream" of a second component, the first component is located nearer to the injector than the second component is to the injector. When used in relation to a component of a fluid delivery system such as a fluid reservoir, a syringe, or a fluid line, the term "downstream" refers to a direction towards the patient and away from the injector of the fluid delivery system. For example, if a first component is referred to as being "downstream" of a second component, the first component is located nearer to the patient than the second component is to the patient.

As used herein, the terms "capacitance" and "impedance" are used interchangeably to refer to a volumetric expansion of injector components, such as fluid reservoirs, syringes, fluid lines, and/or other components of a fluid delivery system as a result of pressurized fluids with such components and/or uptake of mechanical slack by force applied to components. Capacitance and impedance may be due to high injection pressures, which may be on the order of 1200 psi in some angiographic procedures, and may result in a volume of fluid held within a portion of a component in excess of the desired quantity selected for the injection procedure or the resting volume of the component. Additionally, capacitance of various components can, if not properly accounted for, adversely affect the accuracy of pressure sensors of the fluid injector system because the volumetric expansion of components can cause an artificial drop in measured pressure of those components.

The terms "first", "second", and the like are not intended to refer to any particular order or chronology, but refer to different conditions, properties, or elements.

All documents referred to herein are "incorporated by reference" in their entirety.

The term "at least" is synonymous with "greater than or equal to". The term "not greater than" is synonymous with "less than or equal to".

It is to be understood that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a fluid delivery system including at least one valve assembly for preventing delivery of air to a patient. Referring first to FIG. 1, an embodiment of a dual syringe angiography injector system (hereinafter "the fluid delivery system 1000") is illustrated. The fluid delivery system 1000 is configured for injection of two medical fluids through first and second fluid paths 115. A first of fluid paths 115 may be configured to inject a medical fluid, such as an imaging contrast media for an angiography injection procedure, and a second of fluid paths 115 may be configured to inject a flushing fluid, such as saline or Ringer's lactate. The fluid delivery system 1000 may include an injector housing 11 having two syringe ports 15 configured to engage two syringes 12. In some embodiments, the syringes 12 may be retained within corresponding pressure jackets for example to prevent pressure-induced swelling and potential bursting of the syringes 12.

The injector housing 11 may further include at least one graphical user interface (GUI) 16 through which an operator can view and control the status of an injection procedure. The GUI 16 may be in operative communication with a controller 400 (see FIGS. 2-6) which sends and receives commands to and from the GUI 16.

The fluid delivery system 1000 may further include at least one air detector 200 for detecting one or more air bubbles within an air detection region 120 of each fluid path 115. The air detection region 120 may for example, be associated with a proximal portion of each fluid path 115. In some embodiments, the at least one air detector 200 may be a single module having at least one sensor operatively associated with each of the fluid paths 115. In some embodiments, the at least one air detector 200 may include at least two distinct modules, each module operatively associated with one of the fluid paths 115. The at least one air detector 200 may be in operative communication with the controller 400 (see FIGS. 2-6) such that the at least one air detector 200 may send and the controller 400 may receive signals from the at least one air detector 200 indicating the detection of the presence of one or more air bubbles in one or both of fluid paths 115 The at least one air detector 200 may include an ultrasonic sensor, optical sensor, or the like, configured to detect one or more air bubbles within the fluid paths.

Further details and examples of suitable nonlimiting powered injector systems, including syringes, controllers, air detectors, and fluid path sets are described in U.S. Pat. Nos. 5,383,858; 7,553,294; 7,666,169; 8,945,051; 10,022,493; and 10,507,319, the disclosures of which are hereby incorporated by reference in their entireties. While the fluid path elements described herein are illustrated in combination with a fluid injector system including syringes, other fluid delivery mechanisms, such as a pump, for example one or more peristaltic pumps, may be substituted for one or both of the syringes of the fluid delivery systems.

Referring now to FIGS. 2-6 embodiments of the fluid delivery system 1000 further include at least one valve assembly 110. FIGS. 2-6 show a single syringe 12 of the fluid delivery system 1000. For a fluid delivery system 1000 including multiple syringes 12, such as the embodiment shown in FIG. 1, the components shown in FIGS. 2-6 would be duplicated for each syringe 12 of the system (with the possible exception of the controller 400 and actuator 300, which may control the components associated with all of the syringes 12). In addition, for a fluid delivery system 1000 including multiple syringes 12 and thus multiple valve assemblies 100, the patient lines 55 extending from each valve assembly 110 may merge into a single fluid line (not shown) ultimately attached to the patient. In some embodiments, the fluid path assembly may include a fluid mixing connector element to merge fluid flow from each of the syringes 12 and ensure turbulent mixing of the two medical fluids. The fluid mixing connector element may include a mixing element to such as described in International Application No. PCT/US2021/019507, filed Feb. 25, 2021, and U.S. Pat. No. 9,555,379, the disclosures of which are hereby incorporated by reference in their entireties.

Figure 2:
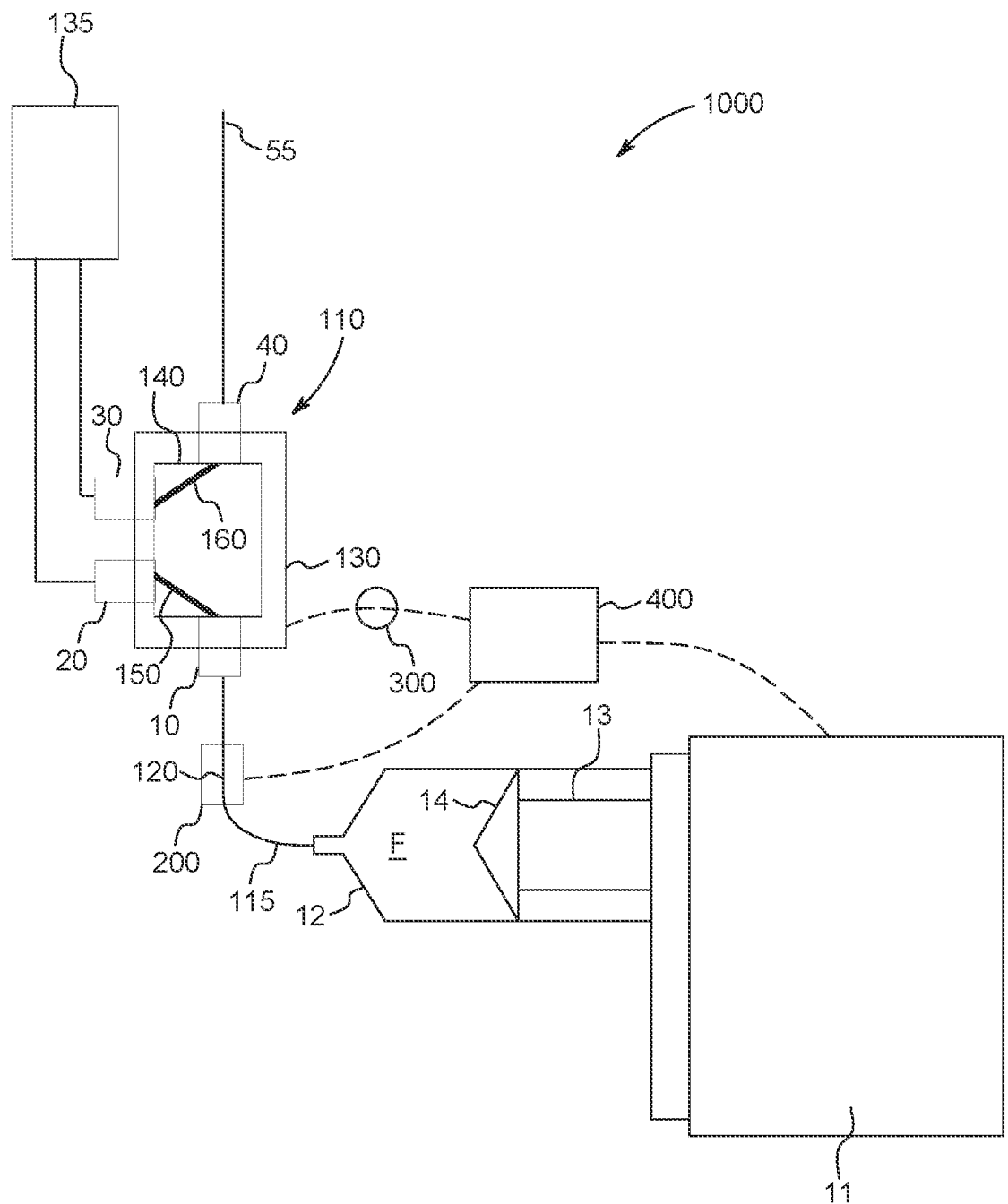
FIG. 2 is a schematic view of a fluid delivery system in accordance with an embodiment of the present disclosure, with a valve assembly thereof in a delivery position.
Figure 3:
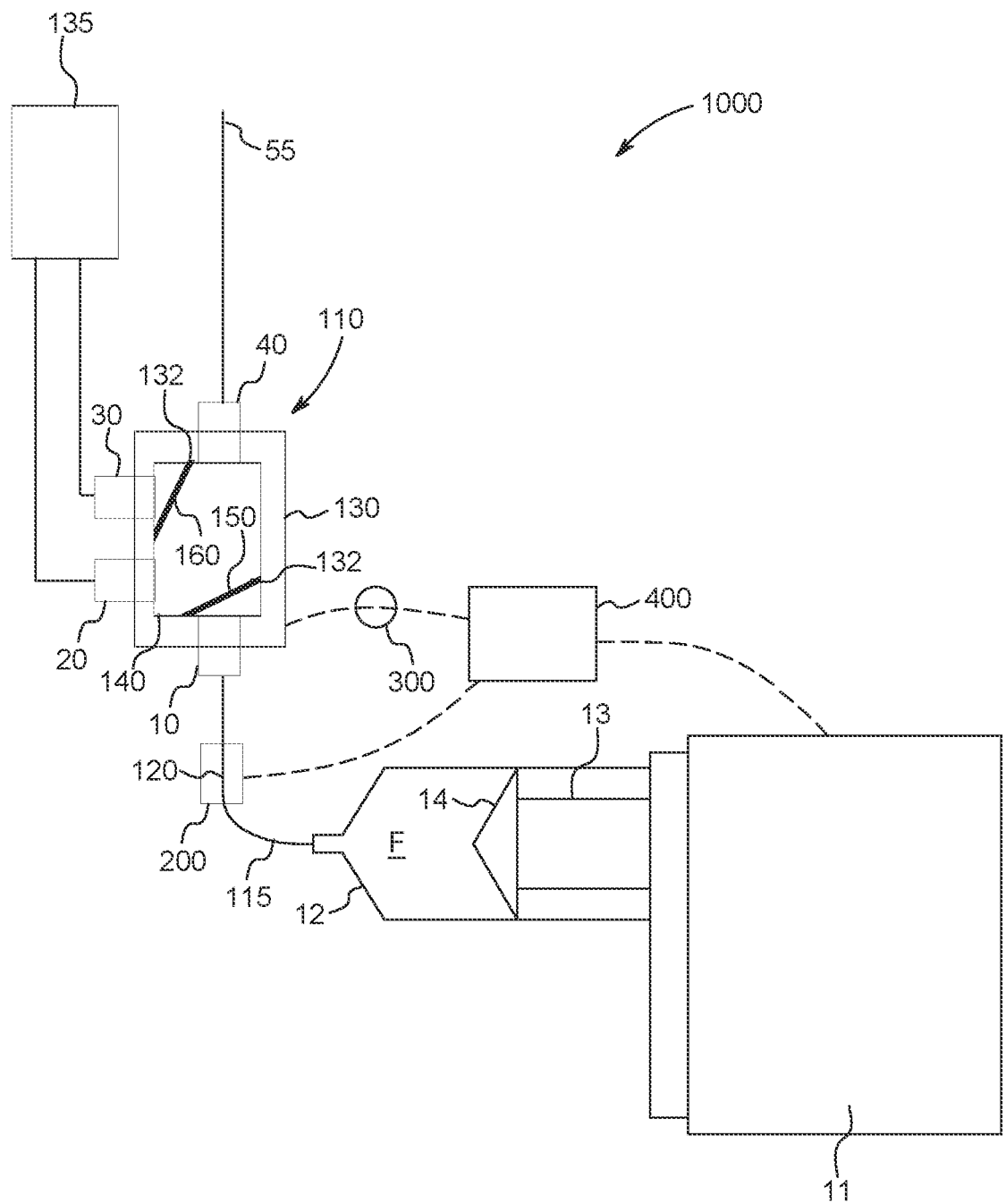
FIG. 3 is a schematic view of the fluid delivery system of FIG. 2, with the valve assembly in a stop position.
Figure 4:
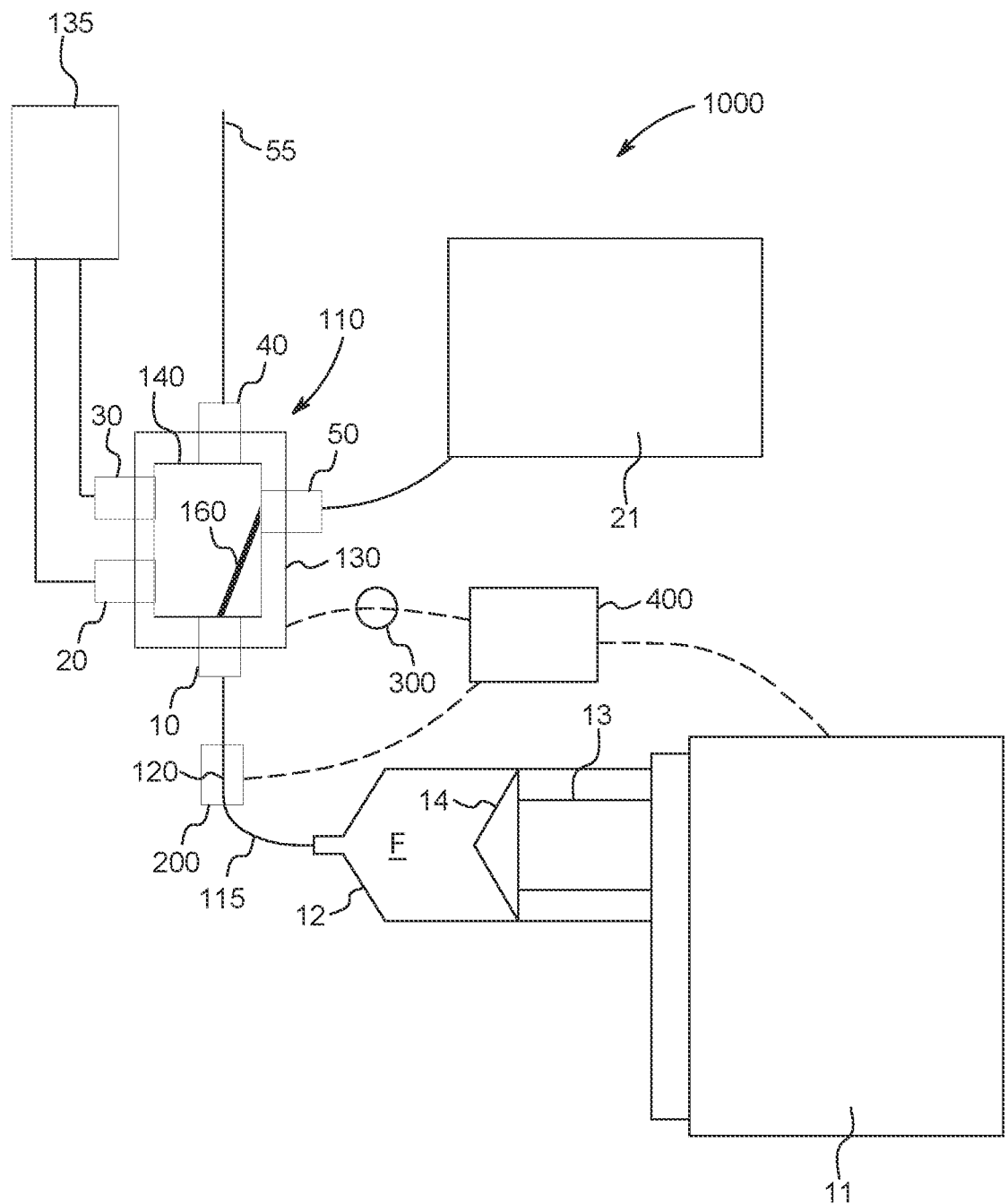
FIG. 4 is a schematic view of the fluid delivery system in accordance with an embodiment of the present disclosure, with a valve assembly thereof in a fill position.
Figure 5:
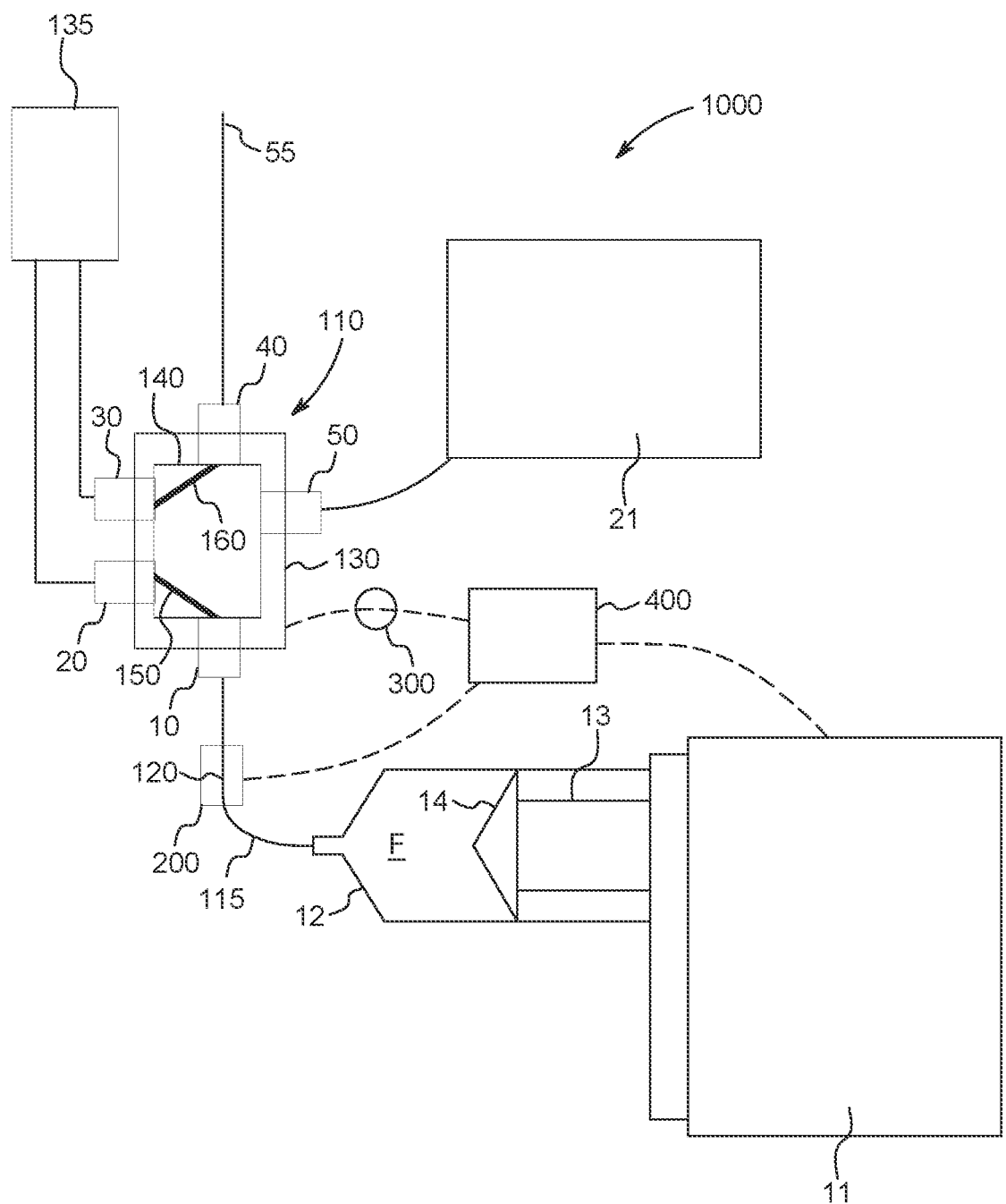
FIG. 5 is a schematic view of the fluid delivery system of FIG. 4, with the valve assembly in a delivery position.
Figure 6:
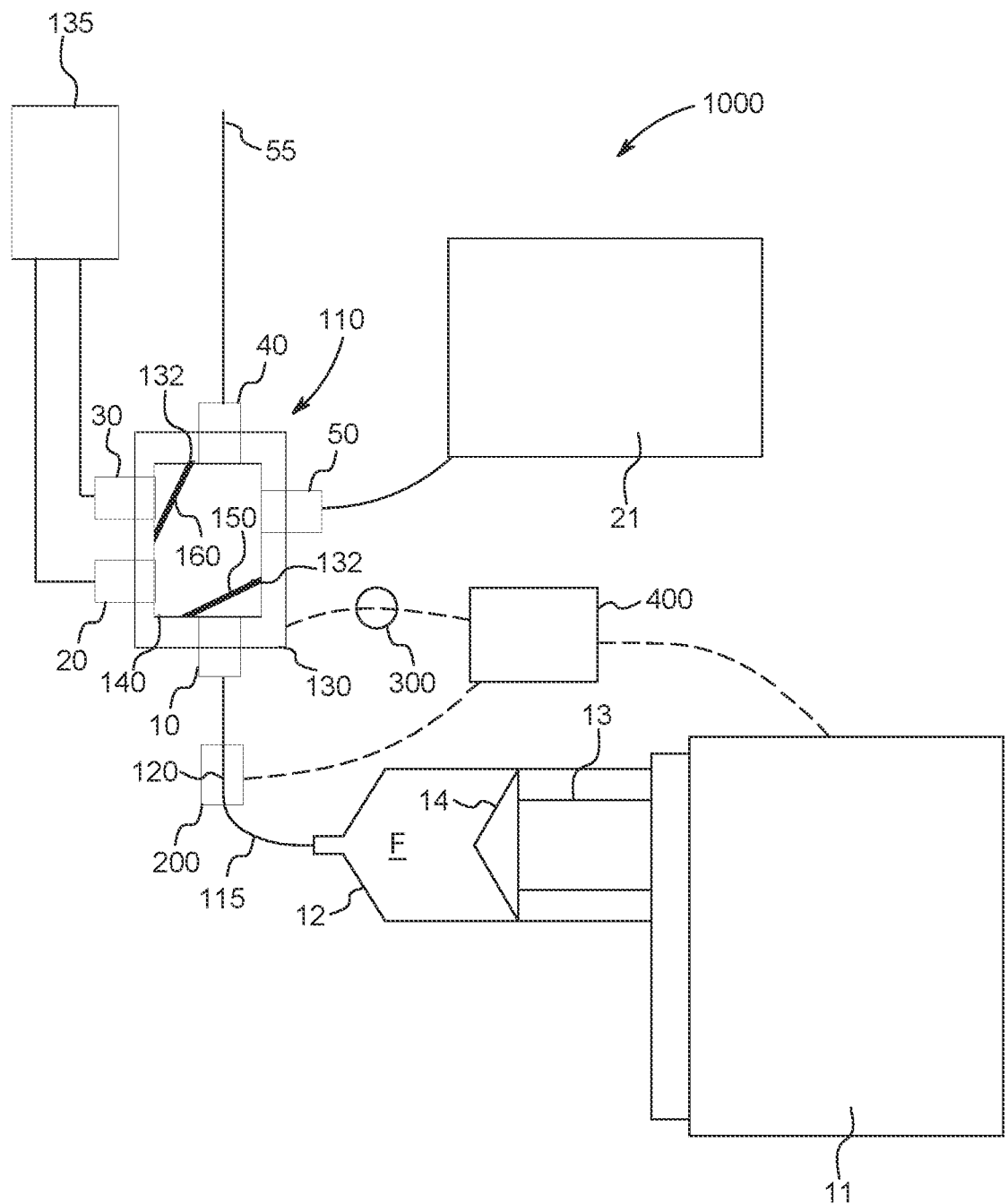
FIG. 6 is a schematic view of the fluid delivery system of FIG. 4, with the valve assembly in a stop position.

Referring first to FIGS. 2 and 3, the valve assembly 110 associated with the syringe 12 includes a plurality of ports, for example a first port 10, a second port 20, a third port 30, and a fourth port 40. Each of the ports is configured for connection and fluid communication with one or more other ports and one or more components of the fluid delivery system 1000 to facilitate fluid flow into, though, and/or out of the valve assembly 110. The first port 10 may be configured for fluid communication with the syringe 12, which injects medical fluid F under pressure into the first port 10 or takes in medical fluid F by applying a vacuum to the fluid through the first port 10. The second port 20 may be configured for fluid communication with a proximal end of a fluid path length 135, and the third port 30 may be configured for fluid communication with a distal end of the fluid path length 135. The fourth port 40 may be configured for fluid communication with a patient line 55 which is in turn connected to a catheter or other device inserted into the vasculature of a patient. In some embodiments, the plurality of ports of the valve assembly 110 may further include a fifth port 50 configured for fluid communication with a bulk fluid container 21 used to fill the syringe 12 with medical fluid F (as shown in FIGS. 4-6).

A controller 400 of the fluid delivery system 100 may be in operative communication with the syringe 12 and may be programmed or configured to actuate (e.g. reciprocally move) a plunger 13 to inject fluid from or take fluid into the syringe 12. More generally, the controller 400 may include at least one processor programed or configured to execute one or more injection procedures according to one or more injection protocols stored in a memory of or accessible by the controller 400.

With continued reference to FIGS. 2 and 3, the valve assembly 110 may include a valve housing 130 and a valve element 140 that are movable relative to one another to provide fluid communication various combination of the plurality of ports. In particular, the valve element 140 may define at least on fluid path providing fluid communication between a pair of the plurality of ports in a first position of the valve housing 130 relative to the valve element 140, and fluid communication between a different pair of the plurality of ports in a second position of the valve housing 130 relative to the valve element 140. Similarly, the at least one fluid path may provide fluid isolation between various ports in the first position and/or the second position of the valve housing 130 relative to the valve element 140, such that fluid cannot flow between the isolated ports. In certain embodiments, the valve element 140 may provide a plurality, for example two, fluid paths providing selective fluid communication between the plurality of fluid ports depending on the relative position of the valve element 140 to the valve housing 130.

Referring in particular to FIG. 2, the valve element 140 may define a first fluid path 150, which, in a delivery position of the valve housing 130 relative to the valve element 140 as illustrated in FIG. 2, provides fluid communication between the first port 10 and the second port 20, thereby allowing fluid communication between the syringe 12 and the proximal end of the fluid path length 135. The valve element 140 may further define a second fluid path 160, which, in the delivery position of the valve housing 130 relative to the valve element 140, provides fluid communication between the third port 30 and the fourth port 40, thereby allowing fluid communication between the distal end of the fluid path length 135 and the patient. Thus, in the delivery position, the first port 10 and second port 20 are in fluid communication via the first fluid path 150, while the third port 30 and the fourth port 40 are in fluid communication via the second fluid path 160. As such, fluid can flow from the syringe 12 into the first port 10, from the first port 10 to the second port 20 via the first fluid path 150, from the second port 20 to the third port 30 via the fluid path length 135, from the third port 30 to the fourth port 40 via the second fluid path 160, and from the fourth port 40 to the patient line 55. The delivery position can thus be used to inject a patient with fluid F from syringe 12.

The valve housing 130 and the valve element 140 may be moved relative to one another from the delivery position shown in FIG. 2 to at least one stop position shown in FIG. 3. In the stop position, for example as illustrated in FIG. 3, the second fluid path 160 may isolate the third port 30 from the fourth port 40 thereby preventing fluid communication and fluid flow to the patient line 55. In particular, the second fluid path 160 may interface with at least one inner wall 132 of the valve housing 130 to prevent fluid flow into and/or out of the second fluid path 160. Similarly, in various embodiments, the first fluid path 150 may interface with an inner wall 132 of the valve housing 130 to prevent fluid flow into and/or out of the first fluid path 150. It is noted that in FIGS. 2-6, the first fluid path 150 and the second fluid path 160 are shown in various orientations for ease of representation; and may not be reflective of the actual orientations of the first fluid path 150 and the second fluid path 160 in preferred embodiments of the present disclosure.

The valve assembly 110 may be moved to the stop position to prevent air from being injected into the patient. For example, the valve assembly 110 may be moved to the stop position when air is detected in the fluid delivery system 1000 upstream of the patient line 55. In particular, an air detector 200, such as an ultrasonic or optical sensor, may be operatively associated with an air detection region 120 along the fluid path 115 or within the first port 10. The air detector 200 may be in operative communication with the controller 400 of the fluid delivery system 1000. The air detector 200 and/or the controller 400 may be configured to detect the presence of one or more air bubbles in the fluid path 115 as the fluid F and air bubbles pass through the air detection region 120. The controller 400 may also be in operative communication with the actuator 300 (e.g. a motor, linear actuator, solenoid, a rotating ball-screw motor, or other electromechanical motor) configured to move the valve assembly 110 between the delivery position, the stop position, and various other positions of the valve assembly 110 described herein. The controller 400 may be programmed or configured to activate the actuator 300 to move the valve assembly 110 to the stop position upon determining that at least one air bubble is present in the air detection region 120. The controller 400 may also be in operative communication with an actuator of the fluid injector system 1000 (e.g. a motor, linear actuator, solenoid, a rotating ball-screw motor, or other electromechanical motor) configured to move the piston 13 and plunger 140 during a fluid injection procedure and may be programmed to stop movement of the piston 13 and plunger 140 during upon detection of at least one air bubble in the air detection region 120. Thus, the fluid injector system 1000 may be configured to detect at least one air bubble in the air detection region 120 and in response the controller 400 may be configured to perform one or more operations that stops the fluid injection procedure (i.e., by halting movement of the piston 13 and plunger 14) and actuating the valve assembly 110 between the delivery position, the stop position, and various other positions of the valve assembly 110.

Because response time of the actuator 300 and movement of the valve assembly 110 from the delivery position to the stop position is not instantaneous, the fluid path length 135 may be configured such that air detected in the air detection region 120 has insufficient time to reach the patient line 55 in the time required for the valve assembly 110 to reach the stop position. In particular, an actuation time of the valve assembly 110 may correspond to a time interval between a time at which the air bubble is detected in the air detection region 120 and a time at which the valve assembly 110 reaches the stop position. Depending on the design of the actuator 300, the actuation time of the valve assembly 110 may be between approximately 60 milliseconds and approximately 100 milliseconds, for example in one embodiment approximately 80 milliseconds, between when one or more air bubble is sensed in the air detection region 120 by the at least one air detector 200 to when the valve actuator may actuate the valve assembly 110 from the delivery position to the stop position to stop a high pressure (e.g. 1200 psi) injection procedure via actuation of the valve assembly 110. In some embodiments, the valve assembly 110 is moved to the stop position while the fluid pressure within the system is still high (e.g. 1200 psi) to prevent expansion of any air bubbles that would occur is a pressure drop was experienced. Even with this rapid response, at the high injection pressures and flow rates utilized during CV angiography injection procedures, the air bubble may still move from 2.8 mL to 3.6 mL of the volume of the fluid path over the 60 milliseconds to 100 milliseconds between detection of an air bubble and the valve assembly 110 reaching the stop position. For example, at approximately 1200 psi with conventional fluid path tubing diameters, an air bubble may travel a distance corresponding to 3.2 mL over 80 milliseconds at a flow rate of 30 mL/sec in a tubing with a 0.072 inch ID. The distance equivalence of 3.2 mL volume for such an embodiment may be approximately 4 feet of tubing length travelled during 80 milliseconds. In view of the distance travelled by the air bubble prior to the valve assembly reaching the stop position, the fluid path length 135 may have sufficient length and/or volume such that an air bubble cannot traverse or expand over the entire length of the fluid path length during the actuation time of the valve assembly 110. As a result, actuation of the valve assembly 110 to the stop position, thereby isolating the patient line 55 from the fluid path length 135, is effective to contain air bubbles within the fluid path length 135 before the air bubbles can be delivered to the patient. Further, if pressurization of the fluid is halted or reduced, the reduction in fluid pressure may result in volume expansion of the air bubble, further increasing the distance the air volume can travel/occupy in the fluid path after a detection event. Thus, the volume of the tubing associated the air detection region and valve assembly 110 must be sufficient to allow the system adequate time to shut the fluid flow to the patient, i.e., by stopping fluid communication between the fourth port 40 before the air bubble can pass through the fourth port 40. The volume of the tubing may be a factor of one or more of inner tubing diameter, length of tubing, pliability or rigidity of the tubing, presence of one or more baffles and combinations thereof associated with the tubing.

In some embodiments, the fluid path length 135 is tubing having a length and associated fluid volume greater than a volume distance than an air bubble can travel or expand during the actuation time taken for the valve assembly 100 to transition from the delivery position to the stop position. For example, the tubing of the fluid path length 135 may be between approximately 1000 millimeters and approximately 1400 millimeters (or between approximately 3.5 feet and approximately 4.5 feet) long. In some embodiments, the tubing of the fluid path length 135 may be approximately 1200 millimeters (or approximately 4 feet) long. In some embodiments, the tubing of the fluid path length 135 may be coiled or wrapped to reduce the size of the fluid path length 135 and to prevent entanglement of the tubing with other components and individuals present in an injection room. The tubing of the fluid path length 135 may be coiled during an extrusion or post-extrusion process, for example where adjacent coils of the coiled length of tubing are adhered or otherwise connected together. In other embodiments, the coils of the coiled length of tubing may be loosely connected together, such as by a tie. In other embodiments, the length of tubing may be coiled or wrapped around a fixture to hold the fluid path length 135 in the coiled configuration. In some embodiments, the fluid path length 135 may include flow disrupting features and/or sections of increased diameter to slow the flow of air bubbles within the fluid path length 135, as described for example in U.S. Provisional Patent Application No. 62/990,179, the disclosure of which is hereby incorporated by reference in its entirety. In other embodiments, the fluid path length 135 may be in a zig-zag configuration extending from the second port 20 to the third port 30 as described herein with reference to FIGS. 27 and 28. The approximately 1000 millimeters to approximately 1400 millimeters (or approximately 3.5 feet to approximately 4.5 feet) length of tubing 135 may be arranged in any manner between the second port 20 and the third port 30, for example, may be stretched lengthwise, draped, wrapped, looped, or coiled to reduce the footprint of the tubing length.

Referring now to FIG. 4, in some embodiments the valve housing 130 and the valve element 140 may be moved relative to one another to a fill position in which fluid is drawn from the bulk fluid container 21 into the syringe 12. In the fill position, the first fluid path 150 or the second fluid path 160 may provide fluid communication between the first port 10 and the fifth port 50 such that fluid may flow from the bulk fluid container 21 to the syringe 12. In certain embodiments, the fill position may also be utilized to prime or purge one or more air bubbles from syringe 12 and the upstream fluid path 115 prior to a fluid injection procedure. The controller 400 may actuate (e.g. retract) the plunger 13 to draw fluid from the bulk fluid container 21 into the syringe 12, for example through fifth port 50, fluid path 160, first port 10, and fluid path 115. The fill position of the valve assembly 110 may be used, for example, prior to an injection procedure to load and/or prime the syringe 12 with the desired type and volume of medical fluid for the injection procedure. FIGS. 5 and 6 illustrate the fluid delivery system 1000 in the delivery position and stop position, respectively, for the embodiment of the valve assembly 110 having the fifth port 50 and bulk fluid source 21 for filling. Operation of the valve assembly 110 in the positions of FIGS. 5 and 6 may be substantially similar as described with reference to FIGS. 2 and 3.

In the various embodiments of the valve assembly 110 described herein, the valve housing 130 and the valve element 140 may be movable relative to one another by any mechanical action, such as rotation or sliding. In some embodiments, the valve housing 130 may be configured to be substantially stationary and the valve element 140 may be configured to be moved relative to the valve housing 130. In some embodiments, the valve element 140 may be configured to be substantially stationary and the valve housing 130 may be configured to be moved relative to the valve element 140. In some embodiments, all of the plurality of ports 10, 20, 30, 40, 50 may be provided on the valve housing 130. In other embodiments, all of the plurality of ports 10, 20, 30, 40, 50 may be provided on the valve element 140. In other embodiments, some of the plurality of ports 10, 20, 30, 40, 50 may be provided on the valve housing 130, and some of the plurality of ports 10, 20, 30, 40, 50 may be provided on the valve element 140. The plurality of ports 10, 20, 30, 40, 50 may be arranged relative to one another in any manner that facilitates the desired fluid communication of the appropriate ports during the fill, delivery, and stop operations described herein. Similarly, the first fluid path 150 and the second fluid path 160 may be arrange in any manner that facilitates communication of the appropriate ports during the fill, delivery, and stop operations described herein.

Having generally and schematically described the components of the fluid delivery system 1000, specific embodiments of the valve assembly 110 and its operation are described.

Referring now to FIGS. 7-16, in some embodiments, the valve assembly 110 may be in the form of a rotary, five-way high-pressure stopcock. It is to be understood that any features not particularly described with reference to FIGS. 7-16 are understood to be identical or similar to the same features described with reference to FIGS. 1-6. As shown in FIGS. 7-16, the valve housing 130 of the five-way high-pressure stopcock 110 may be generally cylindrical in shape, and the plurality of ports (for example the first port 10, the second port 20, the third port 30, the fourth port 40, and the fifth port 50 as described herein) may be spaced circumferentially about the valve housing 130. The valve element 140 may likewise be generally cylindrical in shape, form a fluid tight seal with the valve housing 130, and may rotate about a longitudinal axis relative to the valve housing 130. The plurality of ports may be offset from one another to provide clearance for the first fluid path 150 and the second fluid path 160 of the valve element 140. For example, the first port 10 may be offset relative to the second port 20 along the longitudinal axis of the valve housing 130. The valve element 140 may include an engagement feature 170, such as a bore, boss, tab, gear, etc. for engaging the actuator 300 to facilitate movement of valve element 140 between various positions described herein.

Figure 7:
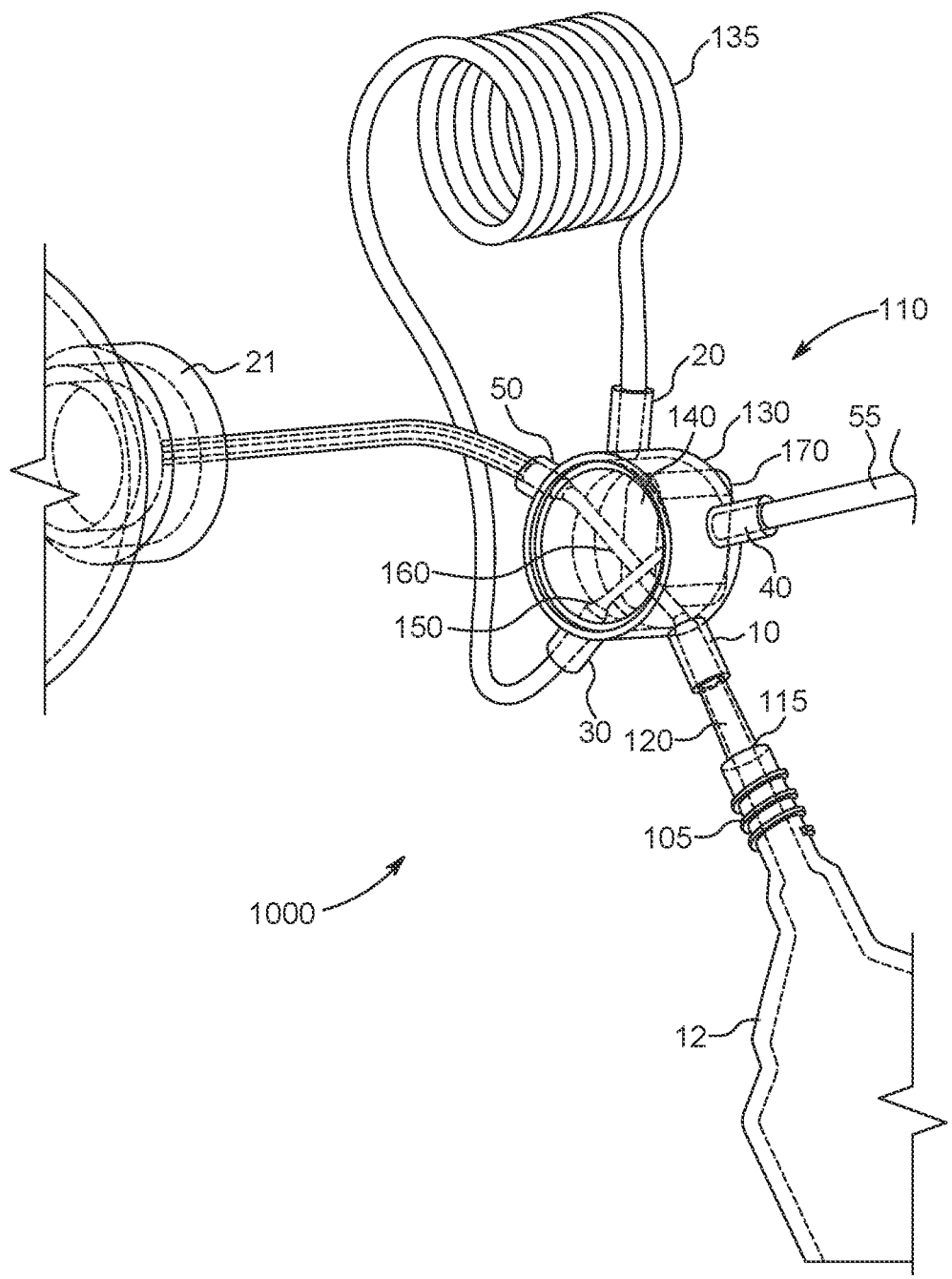
FIG. 7 is a perspective view of a fluid delivery system including a valve assembly according to an embodiment of the present disclosure, with the valve assembly shown in a fill position.

With particular reference to FIG. 7, an embodiment of the fluid delivery system 1000 including the five-way high pressure stopcock 110 is illustrated in a fill position with fluid communication between the fifth port 50 and the first port 10. The five-way high pressure stopcock 110 is attached via the fluid path 115 to a distal connector 105 of the syringe 12. The air detection region 120 may be a portion of the fluid path 115 between the distal connector 105 and the first port 10 of the five-way high pressure stopcock 110 or may be located on the distal connector 105. Alternatively, the air detection region 120 may be a portion of the first port 10. The air detection region 120 is configured to be in operative communication with the air detector 200 (as shown in FIGS. 2-6), such that air detector 200 can detect the presence of one or more air bubbles in fluid path 115 as the fluid passes through air detection region 120.

With continued reference to FIG. 7, the fill position of the five-way high pressure stopcock 110 may provide fluid communication between the first port 10 and the fifth port 50, such that the syringe 12 is fluid communication with the bulk fluid container 21, to allow filling and/or priming of the syringe with a medical fluid during a filling operation. In the fill position, as the plunger 14 (see FIGS. 1-6) associated with the syringe 12 is retracted, fluid flows in sequence from the bulk fluid container 21 through the fifth port 50, the second fluid path 160, the first port 10, and the fluid path 115 into the syringe 12. Also in the fill position, fluid communication between the syringe 12 and downstream components of the fluid delivery system 1000 is blocked to avoid inadvertent injection of fluid and potentially one or more air bubbles into the patient during a filling procedure. That is, the second fluid path 160 providing fluid communication between the first port 50 and the fifth port 50 is the only source of fluid communication with the syringe 12 when in the fill position. The first fluid path 150 of the valve element 140 is not in fluid communication with the syringe 12 or bulk fluid container 21.

Figure 8:
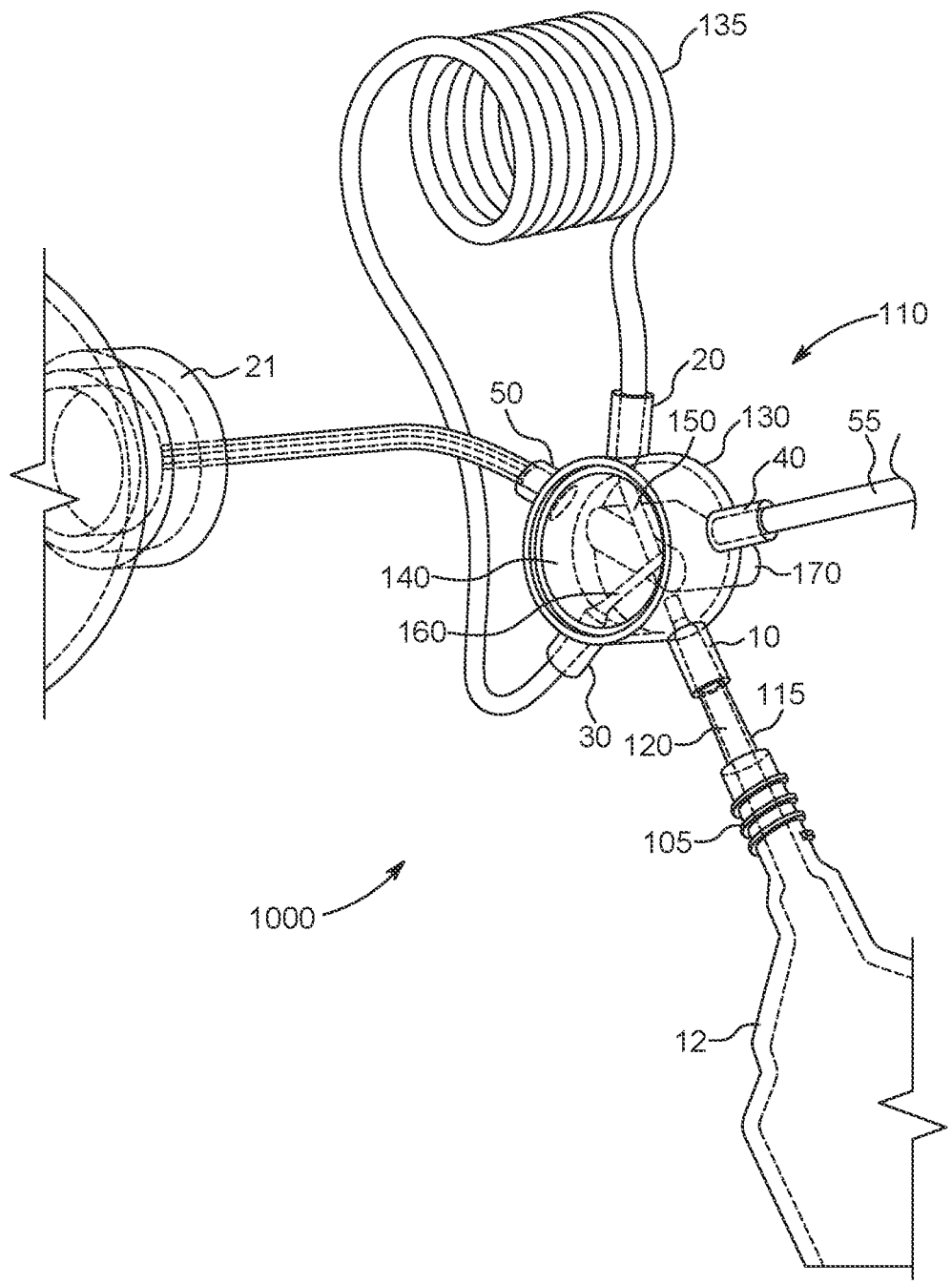
FIG. 8 is a perspective view of a fluid delivery system of FIG. 7, with the valve assembly shown in a delivery position.
Figure 9:
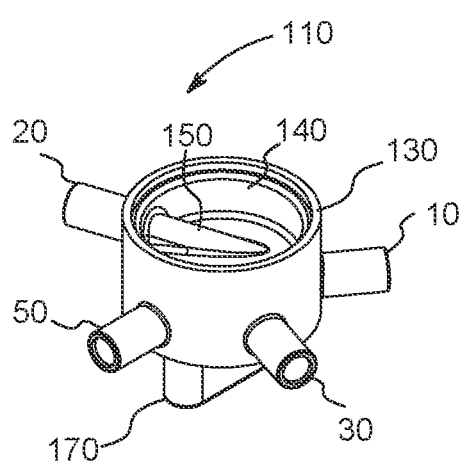
FIG. 9 is a side perspective view of the valve assembly of FIG. 7, with the valve assembly shown in the delivery position.
Figure 10:
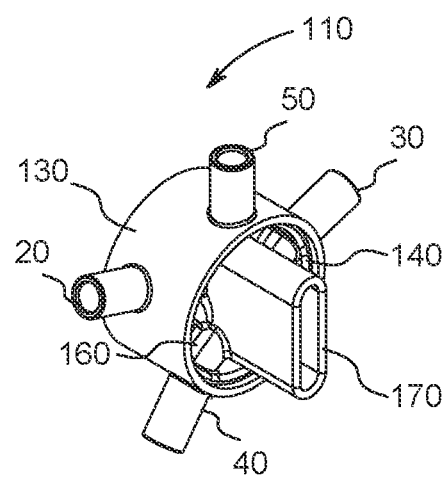
FIG. 10 is a bottom side perspective view of the valve assembly of FIG. 9.
Figure 11:
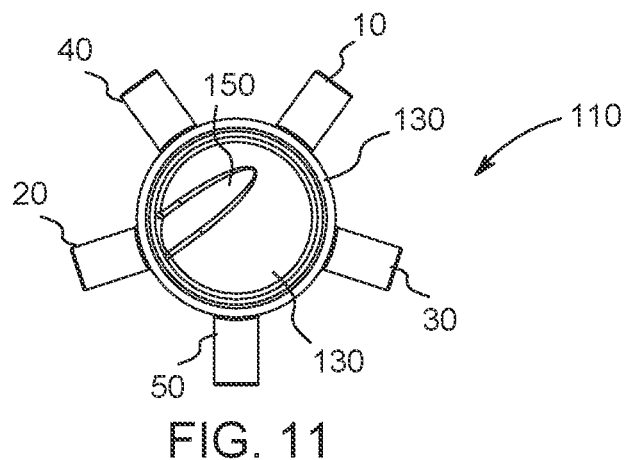
FIG. 11 is a top view of the valve assembly of FIG. 9.

Once the filling operation and subsequent priming operation are completed, the five-way high pressure stopcock 110 may be transitioned to the delivery position shown in FIG. 8 in preparation for an injection procedure. The controller 400 may move the five-way high pressure stopcock 110 to the delivery position by actuating the actuator 300 connected to the engagement feature 170 to rotate the valve element 140 relative to the valve housing 130. In the delivery position, the five-way high pressure stopcock 110 may provide fluid communication between the first port 10 and the second port 20, and fluid communication between the third port 30 and the fourth port 40. As such, fluid injected from the syringe 12 may flow in sequence to the first port 10, the second port 20 via the first fluid path 150, the proximal end of the fluid path length 135 connected to the second port 20, the third port 30 via the fluid path length 135, the fourth port 40 via the second fluid path 160, and finally to the patient line 55. In the fluid delivery position, fluid may flow from the syringe 12 to the patient fluid line 55 over the course of an injection protocol until the total desired volume of medical fluid is delivered to the patient or until at least one air bubble is detected in the upstream air detection region 120, as described herein.

According to some embodiments, the controller 400 is configured to rotate the valve element 140 of the five-way high pressure stopcock 110 to the stop position when air is detected in the fluid path 115 at the air detection region 120 by the air detector 200 (see FIGS. 2-6), thereby and allowing for a rapid shutdown of fluid flow to the patient after detection of at least one air bubble by the air detector 200 even at the high pressures and fluid flow rates associated with angiography. In particular, the volume associated with the fluid path length 135 is sufficiently large enough that the air bubble cannot move from the air detector region 120 through to the fourth port 40 in the time that it takes the air detector 200 to communicate the air detection event to the controller 400 and for the controller 400 to actuate the five-way high pressure stopcock 110 and complete movement of the five-way high pressure stopcock 110 from the delivery position to the stop position, thereby preventing the air bubble from flowing to the patient. If at any time during the injection procedure the controller 400 detects air bubbles in the air detection region 120, the controller 400 may rotate the valve element 140 via the actuator 300 to shut off fluid flow to system components downstream of the fluid path length 135. For example, the valve element 140 may be rotated to a stop position (see e.g. FIG. 6) in which the fourth port 40 is isolated from the third port 30. As such, air bubbles detected in air detection region 120 do not have sufficient time to pass through the volume and length of the fluid path length 135 in the actuation time taken for the valve element 140 to reach the stop position. That is, once an air bubble is detected in fluid path 115, the air detector 200 may transmit a signal to the controller 400 which then activates the actuator 300 to rotate the valve element 140 to the stop position, for example by rotating engagement feature 170. Upon rotation of engagement feature 170, the five-way high pressure stopcock 110 moves to the stop position, stopping fluid flow from the fluid path length 135 to the fourth port 40 and the patient line 55 connected thereto.

In various embodiments of the fluid delivery system 1000 during a high pressure (e.g., up to 1200 psi) injection procedure, after air is initially detected by the air detector 200, it may take from 60 milliseconds to 90 milliseconds, for example in one embodiment approximately 80 milliseconds, for the controller 400 to stop an injection procedure. The total actuation time to stop an injection procedure may include time detecting an air bubble by the air detector 200; time communicating to the controller 400 that an air bubble has been detected; time for the controller 400 instructing the actuator 300 to rotate the five-way high pressure stopcock 110 to a stop position; and time until the patient line 55 is fully isolated from the fluid path length 135 to prevent continued fluid flow from one or more of rapid flow rate, compliance release (i.e., volume relaxation of pressure swollen syringe and fluid path components and release of up-taken mechanical slack in the fluid injector), and/or bubble expansion due to pressure lowering, so as to prevent the air bubble from continuing into the patient. At the high injection pressures typical of CV injection procedures, an air bubble may move from 2.8 mL to 3.6 mL of the volume of the fluid path over the 70 milliseconds to 100 milliseconds between detection of the air bubble and valve closing/injection halting. For example, at approximately 1200 psi, an air bubble may travel a distance corresponding to 3.2 mL over 80 milliseconds at a flow rate of 30 mL/sec in a tubing with a 0.072 inch ID. The distance equivalence of 3.2 mL volume for such an embodiment may be approximately 4 feet of tubing length travelled during 80 milliseconds. Thus, even with a rapid response time, an air bubble may travel a significant distance after air detection and before system shutdown. According to various embodiments of the fluid delivery system 1000 including the five-way high pressure stopcock 110 described herein, the fluid delivery system 1000 may at least temporarily contain the detected air bubble(s) in the fluid path length 135 and prevent the trapped air from being injected into the patient when actuated to the stop position. Upon an air detection event, the fluid injection procedure may be halted upon moving the five-way high pressure stopcock 110 to the stop position and typically the fluid injection and imaging procedure must be rescheduled or reinitiated from the start. It is understood that the volume and length of the fluid path length 135 may be appropriately selected based on injection protocol (i.e., maximum pressure and flow rate) and response time of one or more of the air detector 200, controller 400, actuator 300 of five-way high pressure stopcock 110, and rotational distance necessary to move the valve element 140 to the full stop position.

According to various embodiments, the stop position may be any rotary position of the valve element 140 where the fourth port 40 and the patient line 55 are fluidly isolated from (i.e. not in fluid communication with) either the first fluid path 150 or the second fluid path 160 or both. Because of the relative positions of the first fluid path 150 and the second fluid path 160 of the valve element 140 relative to the fourth port 40, only minor rotational actuation of engagement feature 170 may be required to move the five-way high pressure stopcock 110 from the delivery position to the stop position. For example, the valve element 140 may only need to be rotated so that the second fluid path 160, which is in fluid communication with the fourth port 40 in the delivery position, interfaces with an inner wall 132 of the valve housing 130 not occupied by the fourth port 40.

According to various embodiments, the five-way high pressure stopcock 110 may include an intermediate stop position. In the intermediate stop position, fluid flow within the system is stopped, having a similar or identical effect to the full stop position shown in FIG. 6. To reach the intermediate stop position, the valve element 140 of the five-way high pressure stopcock 110 may be rotated by the actuator 300 to a position relative to the valve housing 130 such that fluid communication between the bulk fluid container 21 and the syringe 12 is blocked. Further, in the intermediate stop position, fluid communication between the syringe 12 and the patient fluid line 55 via fourth port 40 is blocked, for example by blocking fluid communication between the fluid path length 135 at the third port 30 and the patient line 55 connected to the fourth port 40 and/or by blocking fluid communication between the fluid path length 135 at the second port 20 and the syringe 12 connected to the first port 10. The intermediate stop position may allow for all fluid communication within the five-way high pressure stopcock 110 to be ceased without having to transition through another position, such as the fill position or the delivery position. In certain embodiments, the intermediate stop position may be used to prevent pressurized backflow of fluid from a second syringe of the fluid delivery system 1000 (not shown) into the five-way high pressure stopcock 110 and the first syringe 12 or other upstream component of the first syringe fluid path system. For example, if a second syringe is pressurized and in fluid communication, for example, via a downstream fluid mixing connector, with an unpressurized first syringe or a first syringe having a lower fluid pressure, the pressurized fluid from the second syringe may flow upstream into the fluid path components and even the first syringe. In some embodiments, the intermediate stop position may allow pre-pressurization of medical fluid in the syringe 12 prior to moving the five-way high pressure stopcock 110 to the delivery position so that the entire fluid path system is not under the high pressure of the pre-pressurized syringe. This may have the advantage of taking up capacitance in the syringe and components (i.e., accounting for increase fluid volume due to swelling of the syringe and components under high pressure) and/or taking up mechanical slack in the fluid delivery system 1000 to provide a more accurate fluid delivery volume. In other embodiments, pre-pressurization of a medical fluid in syringe 12 may provide smoother pressure/flow transitions when switching between injection of a more viscous medical fluid and a less viscous medical fluid, such as contrast and saline, respectively. Examples of injection protocols using pre-pressurization to prevent fluid flow spikes during fluid transitions are described in International PCT Publication Nos. WO 2019/046260 and WO 2019/046259, the disclosures of which are hereby incorporated by reference in their entireties. In other embodiments, the intermediate stop position may allow for detection of air within the fluid delivery system 1000 by pressurization of the syringe 12 contents prior to the injection procedure, as described in International PCT Publication No. WO 2019/204605, the disclosure of which is hereby incorporated by reference in its entirety. In other embodiments, the intermediate stop position may allow for vacuum coalescence and purging of air bubbles from the syringe system prior to the injection protocol, as described in International PCT Publication No. WO 2019/204617, the disclosure of which is hereby incorporated by reference in its entirety.

While FIGS. 7 and 8 show the fluid path length 135 as a coiled length of tubing, the fluid path length 135 may be any of the various embodiments discussed herein with reference to FIGS. 2-6. For example, the fluid path length 135 may include a length of tubing such as between approximately 1000 and approximately 1400 millimeters, or a length of tubing or approximately 1200 millimeters (or between approximately 3.5 feet and approximately 4.5 feet, or a length of tubing of approximately 4 feet). In some embodiments, such as shown in FIGS. 7 and 8, the tubing of the fluid path length 135 may be coiled to reduce the "footprint" of the fluid path length 135 and allow the fluid delivery system 1000 including the five-way high pressure stopcock 110 to occupy a small amount of space next to the injector housing 11.

Referring now to FIGS. 9 to 16, various views of the five-way high pressure stopcock 110 are provided according to specific embodiments of the present disclosure to more readily illustrate the various fluid flow paths described herein and the interconnectedness of the various ports in different configurations and positions. As described with reference to FIGS. 7 and 8, the valve housing 130 may be rotatably and sealably engaged with the valve element 140, such that fluid even under the high pressure a CV injections cannot flow between the valve housing 130 and the valve element 140 except through the ports 10, 20, 30, 40, 50 and the fluid paths 150, 160. As shown in FIGS. 9-16, the plurality of ports of the five-way high pressure stopcock 110 may be arranged around the periphery of the valve housing 130 in an arrangement that facilitates selective fluid communication between the ports depending on whether the fill position, the delivery position, the stop position, or the intermediate stop position is required. According to an embodiment, the first port 10, the third port 30, the fourth port 40, and the fifth port 50 may be located in a same longitudinal plane around the periphery of the valve housing 130, whereas the second port 20 may be offset towards the top of the valve housing 130 relative to the other ports. The first fluid path 150 may be slanted diagonally relative to the longitudinal axis of the valve housing 130 and/or relative to the planes occupied by the ports 10, 20, 30, 40, 50 in order to provide necessary clearance for the first fluid path 150 and the second fluid path 160 to establish fluid communication with the appropriate ports in the fill position, stop position, and delivery position described herein. The second fluid path 160 may be perpendicular to the longitudinal axis of the valve housing 130, or parallel to the planes occupied by the ports 10, 30, 40, 50.

According to the embodiment shown in FIGS. 9 to 16, in the delivery position, fluid communication is provided between the first port 10 and the offset second port 20 by the diagonal first fluid path 150. As such, fluid communication is provided between the syringe attached to the first port 10 and the fluid path length 135 connected to the second port 20 (see FIG. 8). Also in the delivery position, fluid communication is provided by the second fluid path 160 in the plane between the third port 30 and the fourth port 40. As such, fluid communication is provided between the fluid path length 135 connected to the third port 30 and the patient line 55 connected to the fourth port 40 (see FIG. 8). Also in the delivery position, fluid communication between the fifth port 50 and the first port 10 in blocked, such that the syringe 12 is not in fluid communication with the bulk fluid container 21.

In contrast, in the fill position (see FIG. 7), fluid communication between the first port 10 and the fifth port 50 is provided by the second fluid path 160 in the plane between the first port 10 and the fifth port 50. Also in the fill position, fluid communication is blocked between the third port 30 and the fourth port 40 by the diagonal nature of the first fluid path 150 which does not interconnect the co-planar third port 30 and fourth port 40. Instead, the distal end of the first fluid path 150 abuts an inner wall 132 of valve housing 130 (see FIG. 4).

Figure 12:
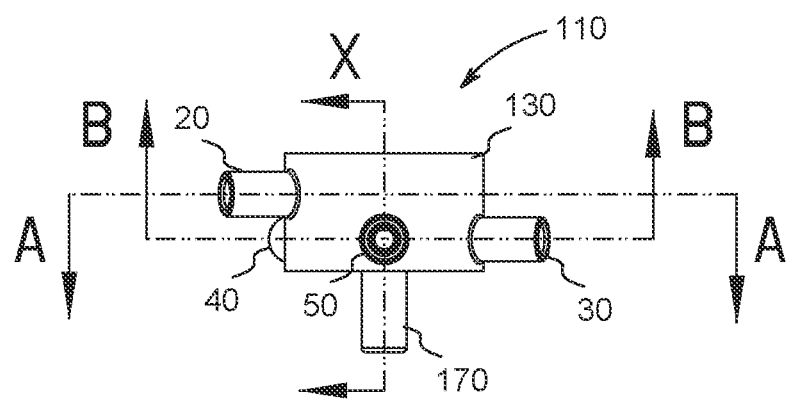
FIG. 12 is a side view of the valve assembly of FIG. 9.
Figure 13:
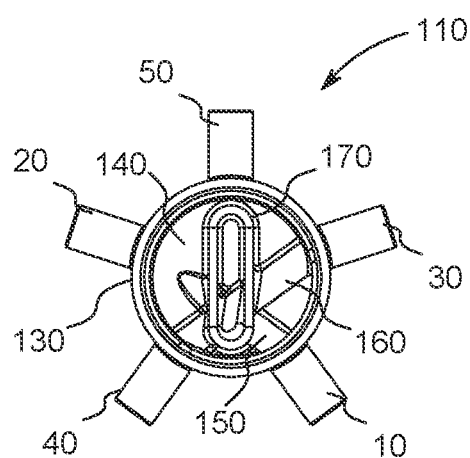
FIG. 13 is a bottom view of the valve assembly of FIG. 9.
Figure 14:
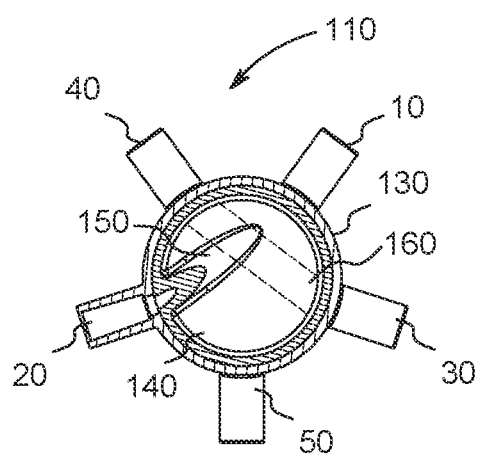
FIG. 14 is a cross-sectional top view of the valve assembly of FIG. 12 along line A-A.
Figure 15:
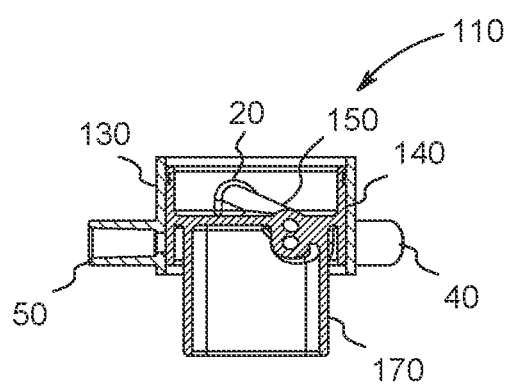
FIG. 15 is a cross-sectional side view of the valve assembly of FIG. 12 along line X-X.
Figure 16:
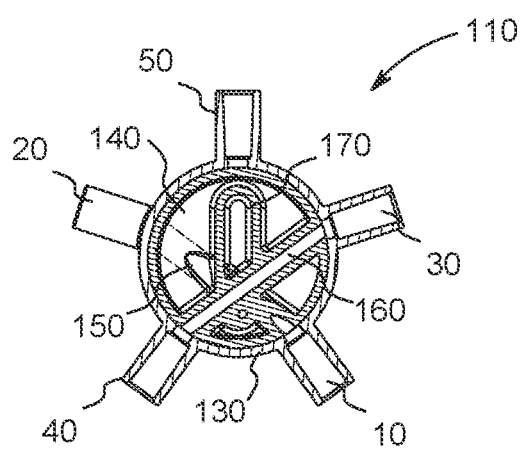
FIG. 16 is a cross-sectional bottom view of the valve assembly of FIG. 12 along line B-B.

Referring specifically to FIGS. 14 to 16, a series of cross-sectional views along the various section lines of FIG. 12 are illustrated in the delivery position. FIG. 14 illustrates a cross-sectional top view of the five-way high pressure stopcock 110 along line A-A of FIG. 12. As shown in FIG. 14, the first fluid path 150 provides fluid communication between the first port 10 and the second port 20. The second fluid path 160 (shown in dashed lines as the second fluid path 160 does not intersect plane A-A) provides fluid communication between the third port 30 and the fourth port 40. FIG. 15 illustrates a cross-sectional side view of the five-way high pressure stopcock 110 along line X-X of FIG. 12. As shown in FIG. 15, fluid communication to the fifth port 50 is blocked in the delivery position. FIG. 16 illustrates a cross-sectional bottom view of the five-way high pressure stopcock 110 along line B-B of FIG. 12. As shown in FIG. 16, the first fluid path 150 provides fluid communication between the first port 10 and the second port 20 (note that the first fluid path 150 is shown in dashed lines near the second port 20 where its diagonal nature leaves plane B-B). The second fluid path 160 provides fluid communication between the third port 30 and the fourth port 40.

Referring now to FIGS. 17-28, in some embodiments of the present disclosure, the valve assembly 110 may be in the form of a high-pressure linear stopcock. It is to be understood that any features not particularly described with reference to FIGS. 17-28 are understood to be identical or similar to the same features described with reference to FIGS. 1-16. Referring first FIG. 17, the valve housing 130 of the high-pressure linear stopcock 110 may be generally cylindrical in shape, and the plurality of ports (for example the second port 20, the third port 30, the fourth port 40, and the fifth port 50) may be arranged along a length of the valve housing 130. In some embodiments, the second port 20, the third port 30, and the fifth port 50 may extend radially from a sidewall of the valve housing 130, and the fourth port 40 may extend from a distal end of the valve housing 130.

The valve element 140 may likewise be generally cylindrical in shape and may be slidable relative to the valve housing 130 along a longitudinal axis relative to the valve housing 130. The valve element 140 may form a fluid tight seal relative to the valve housing 130 via one or more O-rings 116 or elastomeric seals arranged between the valve element 140 and the valve housing 130, for example along the valve element 140 and between the various ports. Further, the one or more O-rings 116 allow the linear stopcock 110 to more readily withstand the high fluid pressures associated with an angiographic injection procedure because the pressures are balanced on each side of the one or more O-rings 116.

The first port 10 configured for connection to the syringe 12 may be provided on (e.g. integrally formed with) a proximal end of the valve element 140, such that the first port 10 moves relative to the other ports (i.e. the second port 20, the third port 30, the fourth port 40, and the fifth port 50) when the valve housing 130 is moved relative to the valve element 140. Further, the first port 10 may be in constant fluid communication with the first fluid path 150 due to the first port being a part of the valve element 140. The air detection region 120 may also be provided directly on, or comprise a portion of, the proximal end of the valve element 140.

Because the syringe 12 of the fluid delivery system 1000 is typically stationary, in some embodiments the valve element 140 connectable to the syringe 12 is also stationary. As such, the actuator 300 moves the valve housing 130 relative to the valve element 140 in order to actuate the high-pressure linear stopcock 110 between the various positions described herein. In other embodiments, the valve element 140 may slide whereas the valve housing 130 remains substantially stationary. As the valve housing 130 slides relative to the valve element 140 (or vice versa), the high-pressure linear stopcock 110 moves between the fill position, the intermediate stop position, the delivery position, and the full stop position as described herein. One or more biasing members and/or motor may be used to actuate high-pressure linear stopcock 110 as described herein.

With continued reference to FIGS. 17-23, the first fluid path 150 and the second fluid path 160 are defined in the valve element 140. At least portions of the first fluid path 150 and the second fluid path 160 path may extend parallel to and/or coaxial with a longitudinal axis of the valve element 140. Further, portions of the first fluid path 150 and the second fluid path 160 extend out of the valve element 140 into the valve housing 130 for communication with the various ports depending on the position of the valve housing 130 and ports relative to the valve element 140 and the corresponding fluid paths 150, 160. As with the embodiments of FIGS. 2-16, the first port 10 of the high-pressure linear stopcock 110 may be configured for connection to a distal connector 105 of the syringe 12, the second port 20 may be configured for connection to a proximal end of the fluid path length 135, the third port 30 may be configured for connection to the distal end of the fluid path length 135, the fourth port 40 may be configured for connection to the patient line 55, and the fifth port 50 may be configured for connection to bulk fluid container 21 (via bulk fluid container line 22 shown in FIGS. 17-20).

Figure 18:
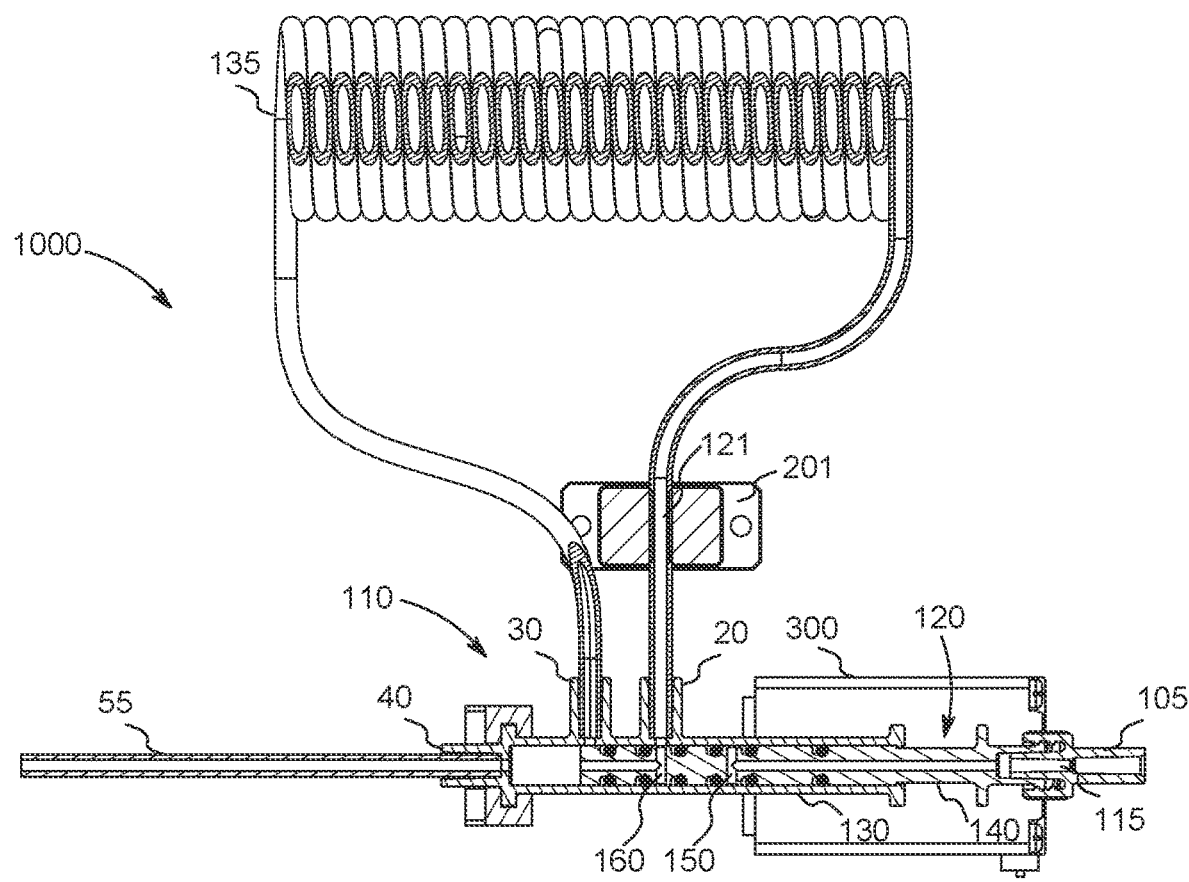
FIG. 18 is a cross-sectional side view of the fluid delivery system of FIG. 17, with the valve assembly in the fill position.
Figure 21:
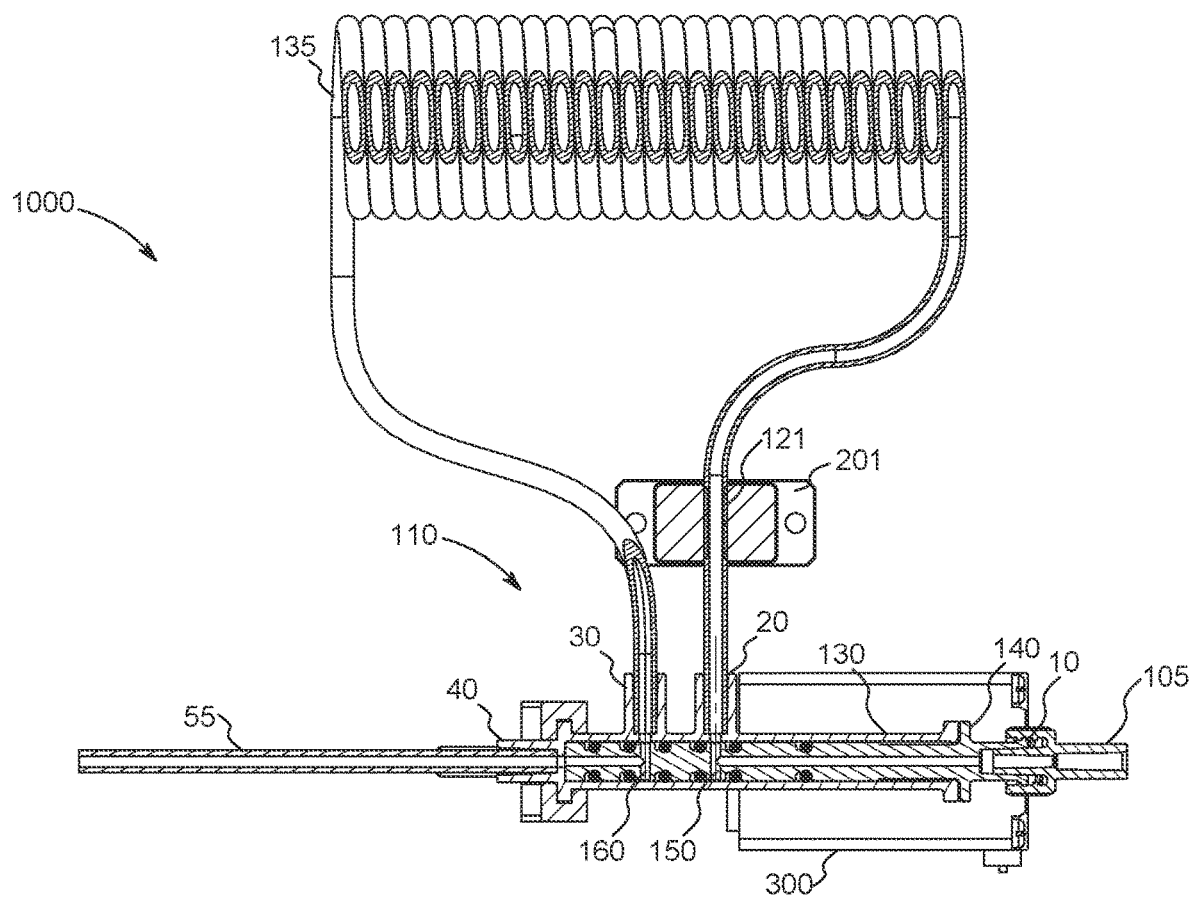
FIG. 21 is a cross-sectional top view of the fluid delivery system of FIG. 20, with the valve assembly in the delivery position.
Figure 23:
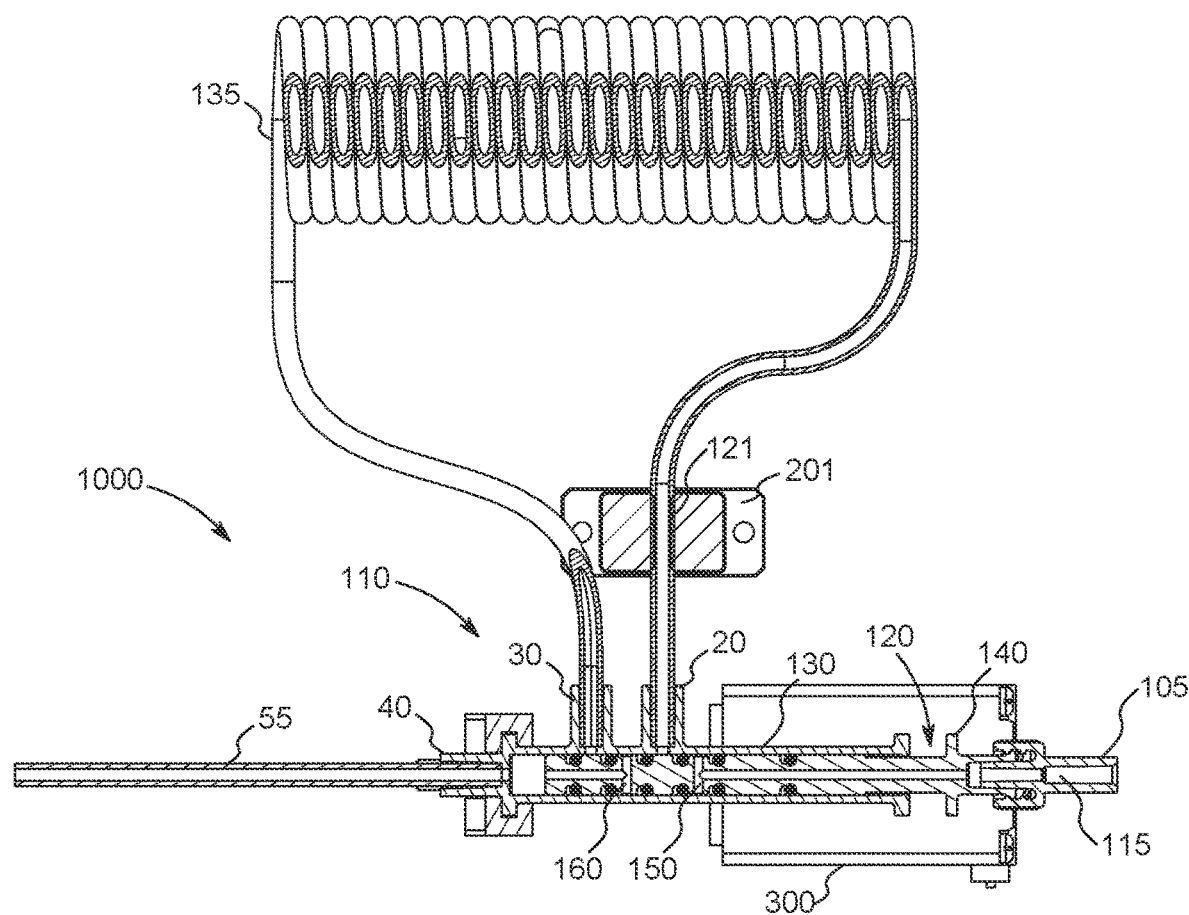
FIG. 23 is a cross-sectional top view of the fluid delivery system of FIG. 17, with the valve assembly in the full stop position.

FIGS. 18, 21, and 23 show an additional air detector 201 and associated air detection region 121. In particular, the air detection region 121 may be a portion of the fluid path length 135 in proximity to the second port 20, such that the air detector 201 may be configured to detect air bubbles flowing into the proximal end of the fluid path length 135. Communication between the air detector 201 and the controller 400 may be substantially the same as communication between the air detector 200 and the controller 400. In some embodiments, the air detector 201 and the air detection region 121 may be provided in addition to the air detector 200 and the air detection region 120. In some embodiments, the air detector 201 and the air detection region 121 may be provided in place of the air detector 200 and the air detection region 120.

With continued reference to FIGS. 17-20, the actuator 300 of the high-pressure linear stopcock 110 includes a biasing member 310, such as a valve spring, which biases the valve housing 130 to the full stop position. The controller 400 (see FIGS. 2-6) may activate the actuator 300 to overcome the bias of the biasing member 310 to hold the valve housing 130 in any of the fill position, the delivery position, or the intermediate stop position. If air is detected by the air detector 200 (see FIGS. 2-6), the controller 400 may be configured to deactivate the actuator 300 such that the biasing member 310 automatically returns the valve housing 130 to the full stop position. The actuator 300 may be an electromechanical motor, such as a solenoid, a rotating ball-screw motor, or other electromechanical motor. The actuator 300 may further include an electromechanical clutch 330 that engages a motor drive assembly 315 with the slidable valve housing 130 and allows the motor to slidably control the valve housing 130 and move the high-pressure linear stopcock 110 between the fill, delivery, full stop, and intermediate stop positions. The electromechanical clutch 330 is in operable communication with the controller 400 and is configured to disengage the motor drive assembly 315 from the slidable valve housing 130 when air is detected in the air detection region 120 by the air detector 200. Disengaging the electromechanical clutch 330 from the motor drive assembly 315 releases the biasing member 310 which then rapidly moves the high-pressure linear stopcock 110 to the full stop position, shutting off fluid flow from the fluid path length 135 to the patient line 55 and preventing the flow of the detected air bubble through the fourth fluid port 40 and into the patient's vasculature system. Alternatively, in certain embodiments, the motor drive assembly 315 may actuate the motor drive assembly 315 to move to the full stop position upon detection of one or more air bubbles in air detection region 120.

In some embodiments, the biased clutch mechanism allows for a rapid shutdown of fluid flow to the patient after detection of at least one air bubble by the air detector 200. For example, in various embodiments of the system 1000 during a high pressure (e.g., 1200 psi) injection procedure, when air is detected by the air detector 200, the valve housing 130 may take from 60 milliseconds to 90 milliseconds, for example approximately 80 milliseconds, to slide the from the delivery position to the full stop position once the actuator 300 is deactivated. Upon activation of the electromechanical clutch 330, the biased valve housing 130 quickly moves to the full stop position, stopping fluid flow from the fluid path length 135 to the patient line 55. The total actuation time to stop an injection procedure may include time detecting an air bubble by the air detector 200; time communicating to the controller 400 that an air bubble has been detected; time for the controller 400 instructing the actuator 300 to release the valve housing 130, the time it takes for the biasing member to move the biased valve housing 130 to the full stop position relative to the valve element 140; and the time until the patient line 55 is fully isolated from fluid path length 135 to prevent fluid continued fluid flow from one or more of rapid flow rate, compliance release and/or bubble expansion from continuing into the patient.

Figure 17:
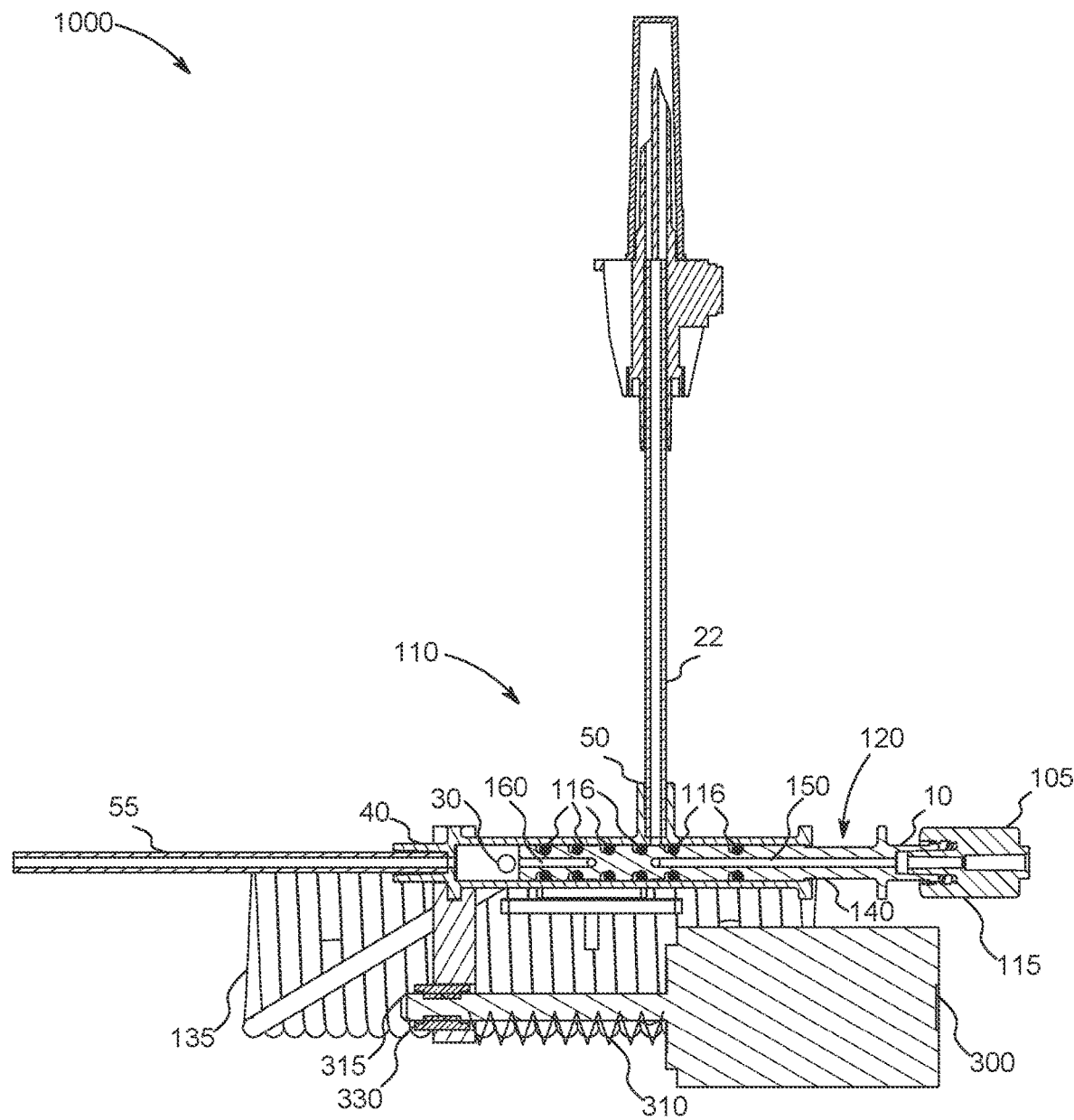
FIG. 17 is a cross-sectional side view of a fluid delivery system including a valve assembly according to an embodiment of the present disclosure, with the valve assembly in a fill position.

Referring particularly to FIGS. 17 and 18, the fill position of the high-pressure linear stopcock 110 is illustrated according to an embodiment of the present disclosure. In the fill position, the valve housing 130 may be in a maximum distal position relative to the valve element 140. In one embodiment, the valve housing 130 is slid relative to the valve element 140 such that the first port 10 is in fluid communication with the fifth port 50 via the first fluid path 150. As such, the syringe 12 is in fluid communication with the bulk fluid container line 22 such that the syringe 12 can draw fluid from the bulk fluid container 21 (see FIGS. 2-6). The second port 20 may be isolated such that no flow into or out of the proximal end of the fluid path length 135 is possible. Also in the fill position, the third port 30 may be in fluid communication with the fourth port 40 due to valve housing 130 being in a distalmost position relative to the valve element 140. However, as the fluid path length 135 is isolated at the second port 20, there is no flow between the third port 30 and the fourth port 40. In other embodiments, the various ports may be configured so that the third port 30 is not in fluid communication with the fourth port 40, when in the fill position.

Figure 19:
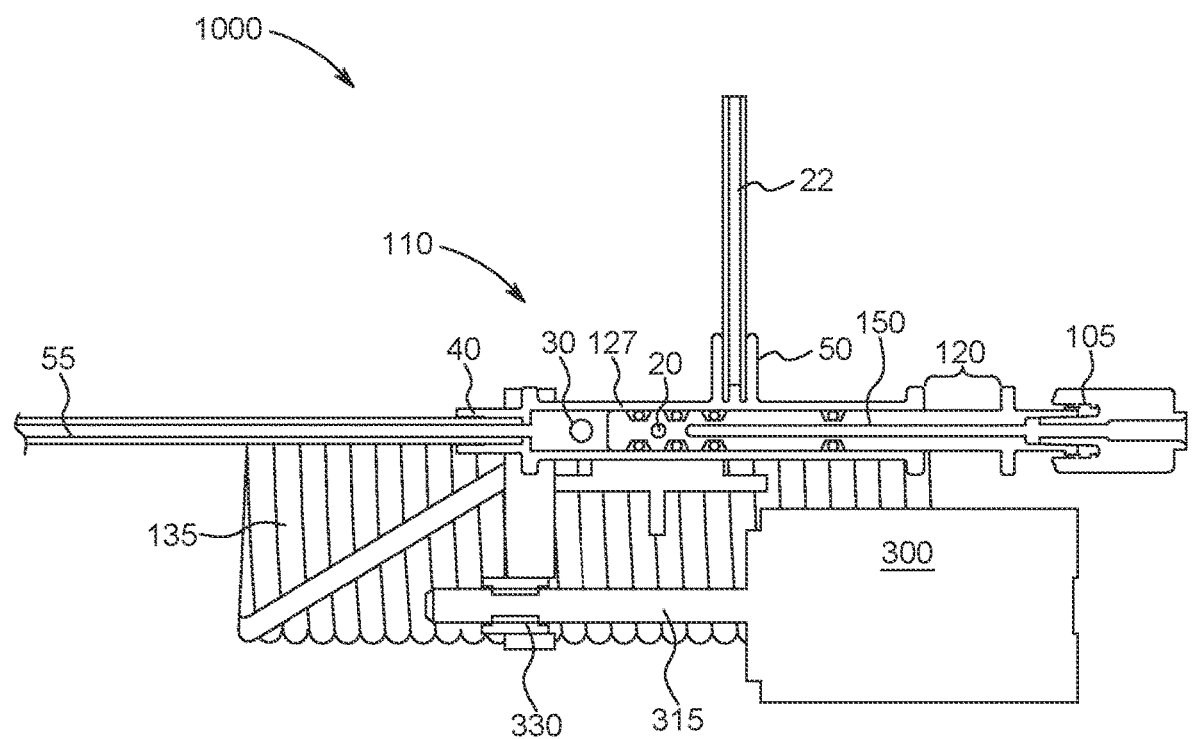
FIG. 19 is a cross-sectional top view of the fluid delivery system of FIG. 17, with the valve assembly in an intermediate stop position.

Referring now to FIG. 19, an intermediate stop position of the high-pressure linear stopcock 110 is illustrated according to an embodiment of the present disclosure. In the intermediate stop position, the valve housing 130 is moved proximally relative to the fill position. In the intermediate stop position, fluid flow within the system is stopped. The valve housing 130 is moved by the actuator 300 to a position relative to the valve element 140 such that fluid communication between the bulk fluid container line 22 and the syringe 12 is blocked. Further, in the intermediate stop position illustrated in FIG. 19, fluid communication between the syringe 12 and the fluid path length 135 through the second port 20 is prevented. In addition or alternatively to stopping fluid communication between the syringe 12 and the fluid path length 135 through the second port 20, fluid communication between the fluid path length 135 and the patient line 55 through third port 30 and/or the fourth port 40 may also be prevented. The intermediate stop position illustrated in FIG. 19 allows for all fluid communication within the high-pressure linear stopcock 110 to be ceased without having to transition through another position, such as the fill position or the delivery position. In certain embodiments, the intermediate stop position may be used to prevent pressurized backflow of fluid from a second syringe into the high-pressure linear stopcock 110 and the syringe 12. In certain embodiments, the intermediate stop position may allow pre-pressurization of a medical fluid in syringe 12 prior to moving the high-pressure linear stopcock 110 to the delivery position. This may have the advantage of taking up capacitance in the syringe and components and/or taking up mechanical slack in the injector system to provide a more accurate fluid delivery volume as described herein. In other embodiments, pre-pressurization of a medical fluid in syringe 12 may provide smoother pressure/flow transitions when switching between injection of a more viscous medical fluid and a less viscous medical fluid, such as contrast and saline, respectively. Examples of injection protocols using pre-pressurization to prevent fluid flow spikes during fluid transitions are described in International PCT Publication Nos. WO 2019/046260 and WO 2019/046259. In other embodiments, the intermediate stop position may allow for detection of air within the syringe system by pressurization of the syringe contents prior to the injection protocol, as described in International PCT Publication No. WO 2019/204605 entirety. In other embodiments, the intermediate stop position may allow for vacuum coalescences and purging of air bubbles from the syringe system prior to the injection protocol, as described in International PCT Publication No. WO 2019/204617.

Figure 20:
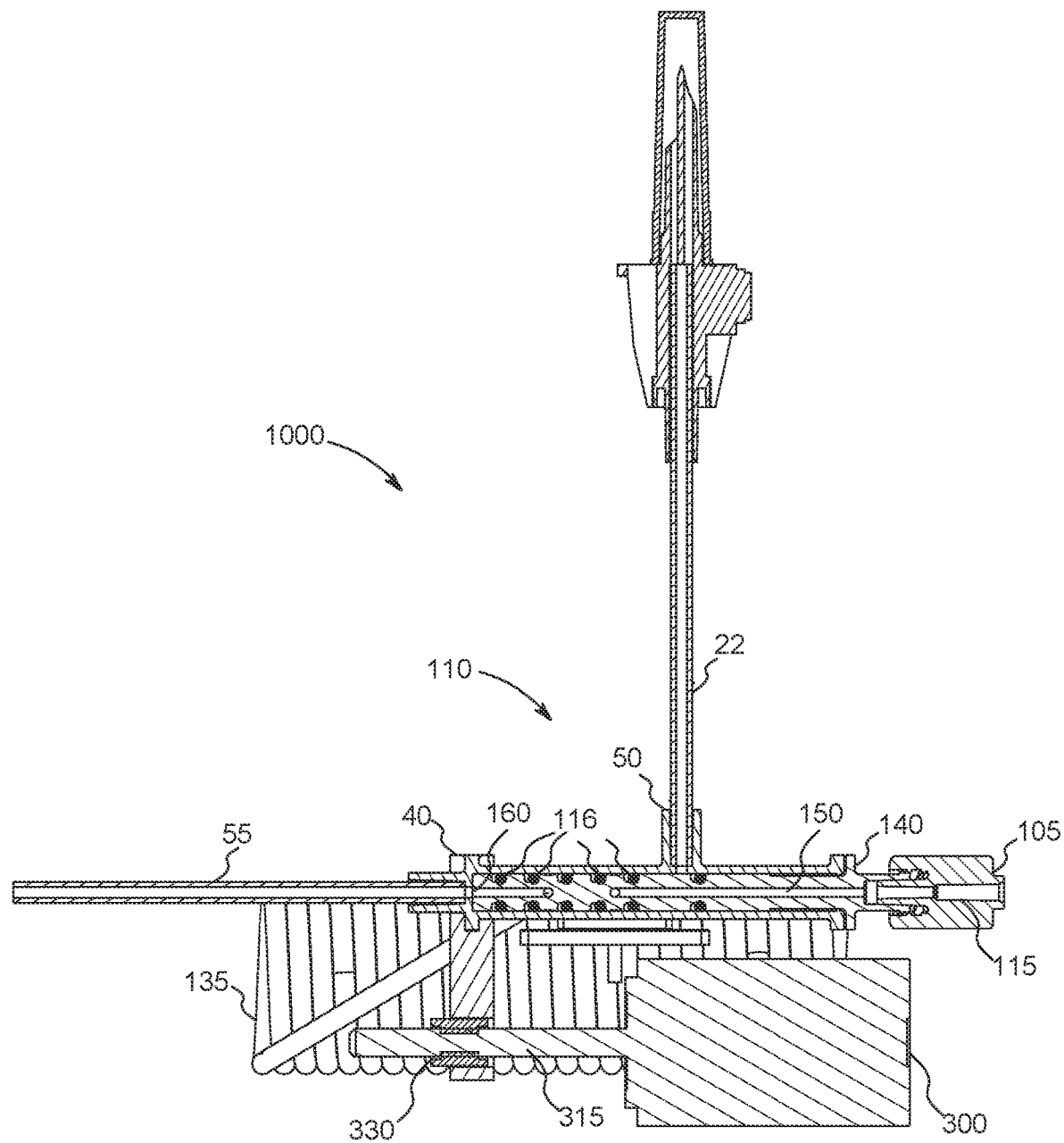
FIG. 20 is a cross-sectional side view of the fluid delivery system of FIG. 17, with the valve assembly in a delivery position.

Referring to FIGS. 20 and 21, the delivery position of the high-pressure linear stopcock 110 is illustrated according to an embodiment of the present disclosure. In the delivery position, the valve housing 130 may be slid farther in the distal direction relative to the intermediate stop position. The valve housing 130 is moved by the actuator 300 to a position relative to the valve element 140 such that fluid communication between the syringe 12 and the patient is provided through the high-pressure linear stopcock 110 and the fluid path length 135. Further, in the delivery position, fluid communication between the bulk fluid container line 22 and the syringe 12 is blocked. Also in the delivery position illustrated in FIGS. 20 and 21, the first port 10 is in fluid communication with the second port 20 via the first fluid path 150. Thus, the syringe 12 is in fluid communication with proximal end of the fluid path length 135. In addition, the third port 30 is in fluid communication with the fourth port 40 via the second fluid path, such that the distal end of the fluid path length 135 is in fluid communication with the patient line 55. As such, fluid injected from the syringe 12 may flow in sequence to the first port 10, the second port 20 via the first fluid path 150, the proximal end of the fluid path length 135 connected to the second port 20, the third port 30 via the fluid path length 135, the fourth port 40 via the second fluid path 160, and finally to the patient line 55. In the delivery position, fluid may flow from the syringe 12 to the patient fluid line 55 over the course of an injection protocol until the total desired volume of medical fluid is delivered to the patient or until at least one air bubble is detected in the upstream air detection region 120, as described herein. In the delivery position of FIGS. 20 and 21, the fifth port 50, and consequently the fluid container line 22, are isolated from the other ports.

Figure 22:
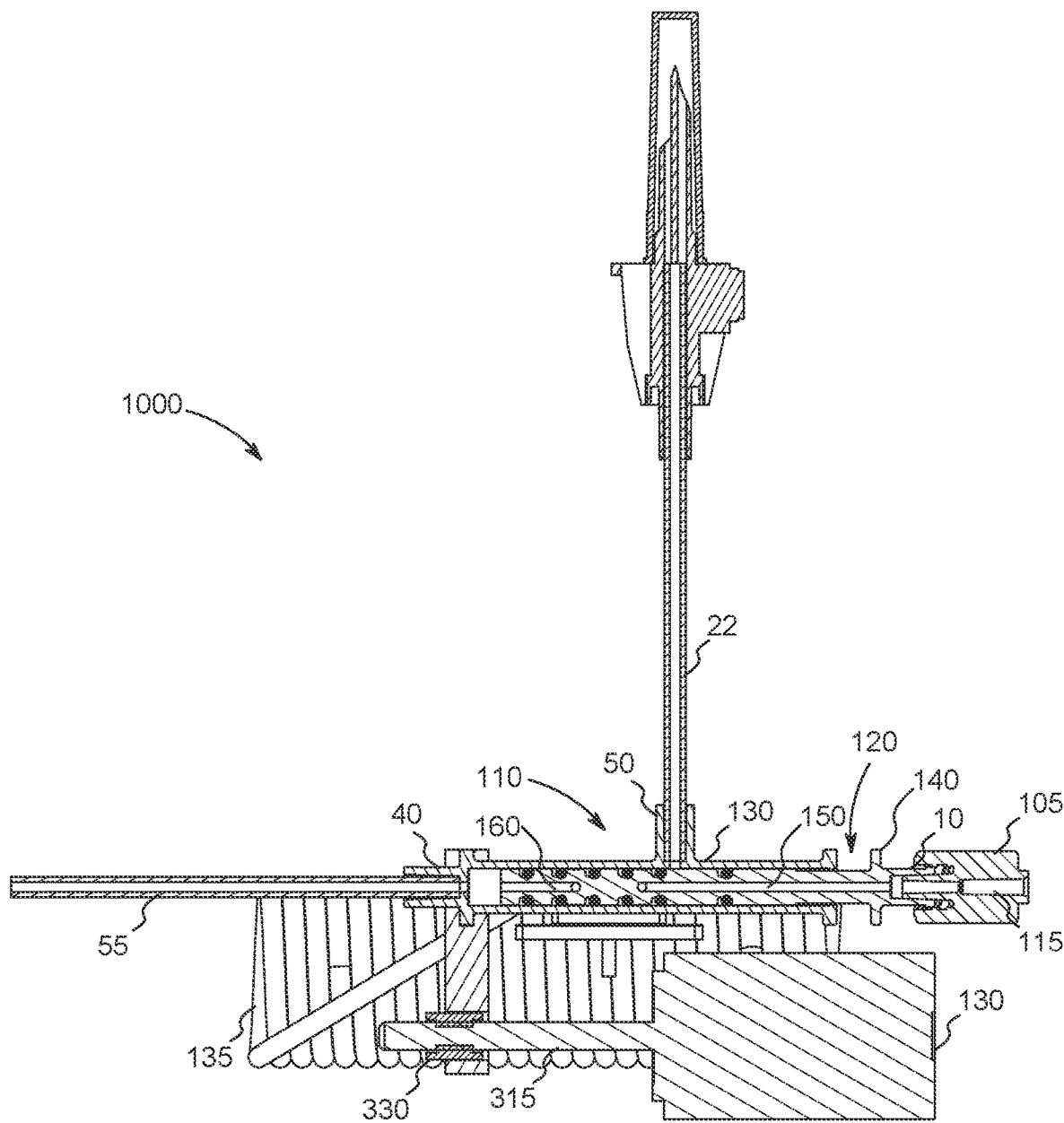
FIG. 22 is a cross-sectional side view of the fluid delivery system of FIG. 17, with the valve assembly in a full stop position.

Referring now to FIGS. 22 and 23, the full stop position of the high-pressure linear stopcock 110 is illustrated according to an embodiment of the present disclosure. In the full stop position, the valve housing 130 may be slid to a maximum proximal position relative to the valve element 140. In the full stop position, the valve housing 130 is moved to a position relative to the valve element 140 such that fluid communication between the fluid path length 135 through the port 30 into the patient line 55 is stopped, thereby preventing further fluid flow and potential delivery of one or more air bubbles to the patient. The valve housing 130 is moved to the full stop position by disengaging the electromechanical clutch 330 from the motor drive assembly 315, allowing the biasing force from biasing member 310 to slide the valve housing 130 to the full stop position. As described herein, disengagement of the clutch 330 is activated by the controller 400 upon detection by the air detector 200 of at least one air bubble in the air detection region 120.

Referring now to FIGS. 24-26, an embodiment of a high-pressure linear stopcock 610 that is not connected to other injector or disposable features is shown. The high-pressure linear stopcock 610 of FIGS. 24-26 may be functionally similar or identical to the high-pressure linear stopcock 110 of FIGS. 17-23. However, the high-pressure linear stopcock 610 does not include the actuator 300, the fluid path length 135, and other fluid path components that form a part of the high-pressure linear stopcock 110. The high-pressure linear stopcock 610 includes a valve housing 630 that is rapidly movable relative to a valve element 640, in the same manner as the valve housing 130 and the valve element 140 of the high-pressure linear stopcock 110. The high-pressure linear stopcock 610 includes a first port 611 configured for connection to a syringe (not shown); a second port 612 configured for connection to a proximal end of an fluid path length, such as a length of tubing (not shown); a third port 613 configured for connection to a distal end of the fluid path length; a fourth port 614 configured for connection to a patient line (not shown), and a fifth port 615 configured for connection to a bulk fluid container (not shown). The ports 611, 612, 613, 614, and 615 may be arranged on the high-pressure linear stopcock 610 and may function similarly or identical to the plurality of ports 10, 20, 30, 40, and 50, respectively, of the high-pressure linear stopcock 110. Each of ports 611, 612, 613, 614, and 615 may be in the form of a connector, such as a Luer connector, a bayonet connector, or the like, to facilitate connection to their associated fluid path components. Other connector designs suitable for use on the various fluid path components are described in PCT International Application No. PCT/US2021/018523, the disclosure of which is incorporated by this reference in its entirety.

FIG. 25 illustrates an end-on view of the distal end of the high-pressure linear stopcock 610, showing the fourth port 614 and the third port 613. FIG. 26 is a cross-section view along line C-C of FIG. 25. According to the illustrated embodiment, the high-pressure linear stopcock 610 is attachable to the distal end of a syringe 12 of a high-pressure fluid injector, such as shown in FIG. 1. In particular, the syringe 12 may be connected to the first port 611 of the high-pressure linear stopcock 610. The high-pressure linear stopcock 610 includes an air detection region 620 at the proximal portion of the high-pressure linear stopcock 610, analogous to the air detection region 120 of the high-pressure linear stopcock 110 and configured to be placed in operative communication with air detector 200 as described herein.

With continued reference to FIGS. 25 and 26, the valve element 640 of the high-pressure linear stopcock 610 may be substantially identical to the valve element 140 of the high-pressure linear stopcock 110. In particular, the valve element 640 may define a first fluid path 650 and a second fluid path 660 that provide selective fluid communication between the ports 611, 612, 613, 614, and 615. One or more O-rings 616 provide a fluid tight seal between the valve element 640 and the valve housing 630 while allowing the valve housing 630 to slide relative to the valve element 640. In certain embodiments, the valve housing 630 may slide whereas the valve element 640 is held substantially stationary. As the outer housing 130 slides relative to the valve element 640, the high-pressure linear stopcock 110 moves between the fill position, the intermediate stop position, the delivery position, and the full stop position in essentially the same manner as the high-pressure linear stopcock 110 of FIGS. 17-23. In other embodiments, the valve element 640 may slide whereas the valve housing 630 is held substantially stationary.

The high-pressure linear stopcock 610 may be activated by an actuator 300 in operative communication with a controller 400 in the same manner described in connection with the high-pressure linear stopcock 610. That is, the high-pressure linear stopcock 610 is operated by an actuator 300 and a biasing member 310, such as a valve spring, which is biased to the full stop position but can be held one in any of the fill position, the delivery position, or the intermediate stop position by the actuator 300. Disengaging an electromechanical clutch 330 from a motor drive assembly 315 of the actuator releases the biasing member 310 which then rapidly moves the high-pressure linear stopcock 610 to the full stop position, shutting off fluid flow from the fluid path length 135 and the patient line 55.

Figure 27:
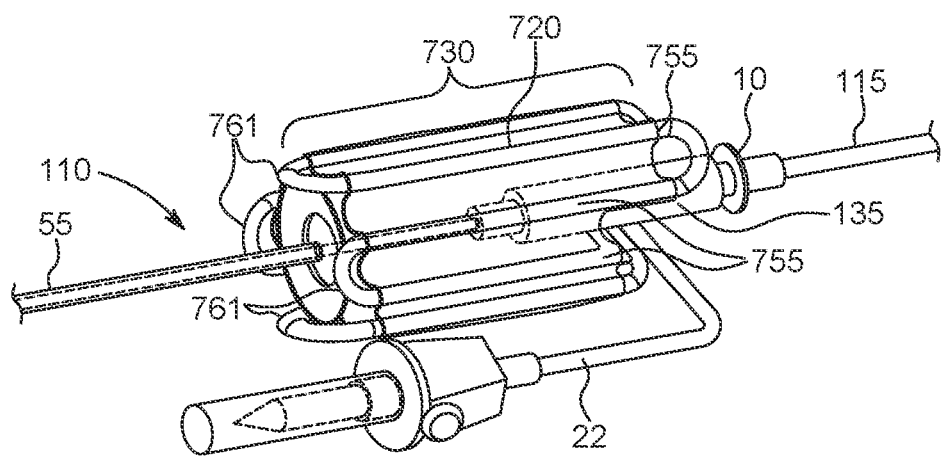
FIG. 27 is a perspective view of a fluid delivery system including a valve assembly according to an embodiment of the present disclosure.
Figure 28:
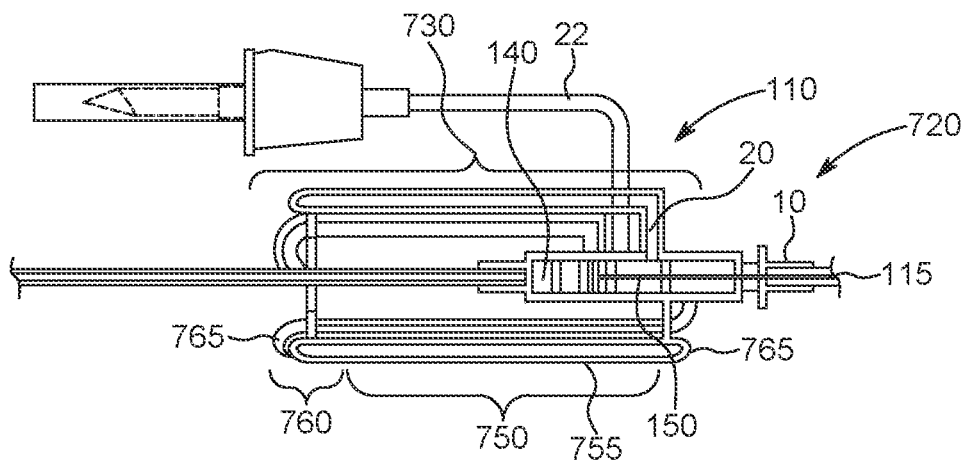
FIG. 28 is a cross-sectional side view of the fluid delivery system of FIG. 27.

FIGS. 27 and 28 illustrate an embodiment of the high-pressure linear stopcock 110 similar to that of FIGS. 17 to 26, but in which the fluid path length 135 at least partially circumferentially surrounds the valve housing 130. As many of the components and the functionality of the embodiment of FIGS. 27-28 are similar or identical to the embodiment of FIGS. 17-26, only the differences will be discussed below. As shown in FIGS. 27 and 28, the fluid path length 135 may be a fluid path element 720 having a cylindrical zig-zag fluid path 730. The fluid path element 720 may be configured to surround the valve housing 130 in a cylindrical manner or other shape, such as a rectangular box-like structure, conical arrangement, etc. The fluid path 730 of the fluid path element 720 may be a zig-zag fluid path having a plurality of substantially longitudinal fluid channels 755 arranged about the valve housing 130 and a plurality of bent fluid channels 765 connecting the plurality of longitudinal fluid channels 755 in series. The plurality of longitudinal fluid channels 755 may be arranged in a tubing bundle 750 formed of a single, integral unit or multiple sections. The plurality of bent fluid channels 765 may be in the form of two end caps 760 applied to opposite ends of the bundle 750 of the longitudinal fluid channels 755, such that each of the bend fluid channels 765 provides fluid communication between two adjacent longitudinal fluid channels 755. Each of the bent fluid channels 765 may include up to a 180 degree turn to facilitate connection of the longitudinal fluid channels 755. In various embodiments, the two end caps 760 may be configured to be bonded to opposite open ends of the tubing bundle 750. According to various embodiments, each of the bent fluid channels 765 may direct fluid flow from an end of one of the longitudinal fluid channels 755 to an adjacent longitudinal fluid channel 755 of the bundle 750, creating the cylindrical zig-zag fluid path 730. Each end cap 760 may be bonded to opposite ends of the tubing portion 750, for example, by adhesion, welding, solvent welding, laser welding, and the like. In certain embodiments, the plurality of longitudinal fluid channels 755 of the fluid path element 720 may be substantially straight and parallel to one another, whereas in other embodiments, the longitudinal fluid channels 755 may be in a configuration that is not parallel but nevertheless reduces the overall footprint of the fluid path element 720.

Figure 29:
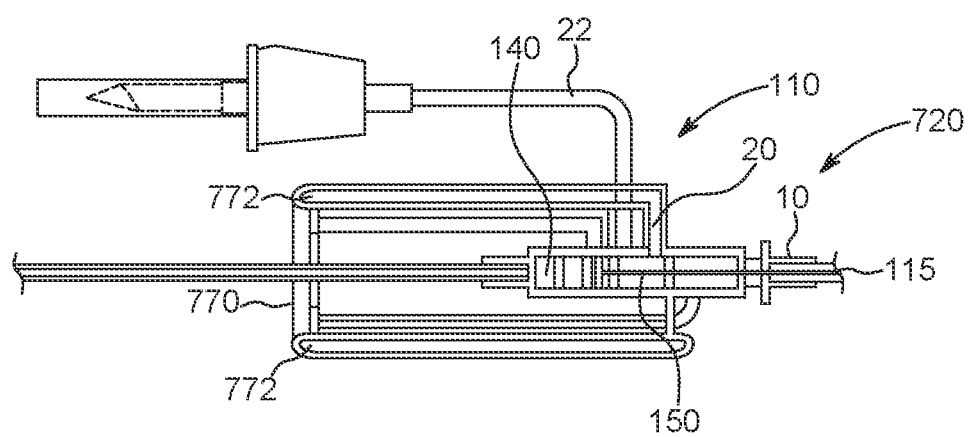
FIG. 29 is a cross-sectional side view of a fluid delivery system including a valve assembly according to an embodiment of the present disclosure.

Referring now to FIG. 29, in another embodiment, the fluid path length 135 may be a hollow cylinder 770 wrapped around the valve housing 130 and defining an internal chamber 772. A cross section of the internal chamber 772 may be annular or ring shaped with the valve housing 130 extending through the center of the internal chamber 772. The internal chamber 772 may be in fluid communication with the second port 20 and the third port 30, in essentially the same manner as the tubing bindle 750 of FIGS. 27-28. The internal chamber 772 may have a total volume greater than a volume that an air bubble can travel or expand in the actuation time of the high pressure linear stopcock 110. In some embodiments, the internal chamber 772 may have a total volume of between approximately 2.8 mL and approximately 3.6 mL, and in specific embodiments approximately 3.2 mL. Air bubbles detected by air detector 200 in the air detection region 120 are thus contained in the internal chamber 772 while the high pressure linear stopcock 110 is actuated from the delivery position to the full stop position (or to the intermediate stop position), thereby preventing the air bubbles from reaching the third port 30 and being injected into the patient.

As described herein, in various embodiments, the total volume and/or or length of the fluid path length 135 may be a length calculated to ensure that an air bubble detected by the air detector 200 cannot flow or expand through the entirety of the fluid path length 135 in the actuation time taken by high-pressure linear stopcock 110 to reach the stop position. As such, in certain embodiments, the total length of tubing of the fluid path 730, including all of the longitudinal fluid channels 755 and the bent fluid channels 765, may be from approximately 1000 millimeters to approximately 1400 millimeters and in specific embodiments may be approximately 1200 millimeters (or from approximately 3.5 to approximately 4.5 feet and in specific embodiments, may be approximately 4 feet).

The various fluid path tubing elements according to the various embodiments described herein may be configured to further reduce a footprint of the tubing between the air bubble sensing region 120 and valve element, for example to reduce the space occupied the tubing in an injection suit, reduce packaging size, increase ease of handling, reduce disposal volume, increase ease of manufacture, etc. while still providing sufficient volume and length to allow actuation of the valve element and prevent further flow of an air bubble into a patient after an upstream air detection event.

While various examples of the present invention were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

We claim:

1. A valve assembly for a fluid injector system, the valve assembly comprising:
   a valve housing;
   a first port configured for fluid communication with at least one syringe of a fluid injector, a second port, a third port, and a fourth port configured for fluid communication with a patient line;
   a fifth port configured for fluid communication with a bulk fluid source;
   an air detection region associated with the first port;
   a fluid path length having a proximal end in fluid communication with the second port and a distal end in fluid communication with the third port; and
   a valve element defining a first valve fluid path and a second valve fluid path, wherein the first valve fluid path provides fluid communication between the first port and the second port when in a delivery position of the valve housing relative to the valve element,
   wherein the second valve fluid path provides fluid communication between the third port and the fourth port when in the delivery position,
   wherein the third port is isolated from the fourth port when in a stop position of the valve housing relative to the valve element, and
   wherein the first fluid path provides fluid communication between the first port and the fifth port when in a fill position of the valve housing relative to the valve element.

2. The valve assembly of claim 1, wherein the fluid path length comprises tubing having a length greater than a distance that an air bubble can travel or expand during an actuation time of the valve assembly, and wherein the actuation time of the valve assembly is a time interval between a time at which the air bubble is detected in the air detection region and a time at which the valve assembly reaches the stop position.

3. The valve assembly of claim 1, wherein the fluid path length comprises tubing have a length of between approximately 1000 millimeters and approximately 1400 millimeters.

4. The valve assembly of claim 1, wherein the first port, the second port, the third port, and the fourth port are arranged circumferentially about the valve housing and wherein the valve element is rotatable about a longitudinal axis of the valve housing between the delivery position and the stop position.

5. The valve assembly of claim 1, wherein the first port is offset relative to the second port along a longitudinal axis of the valve housing.

6. The valve assembly of claim 1, wherein the fluid path length comprises coiled tubing.

7. A fluid delivery system comprising:
   at least one powered injector;
   at least one syringe;
   at least one air detector;
   a valve assembly;
   at least one controller in electrical communication with the at least one air detector, wherein the at least one controller is configured for controlling fluid flow through the valve assembly; and
   a patient line,
   a bulk fluid source,
   wherein the valve assembly comprises:
      a valve housing;
      a first port in fluid communication with the at least one powered injector, a second port, a third port, and a fourth port;
      a fifth port in fluid communication with the bulk fluid source;
      a fluid path length having a proximal end in fluid communication with the second port and a distal end in fluid communication with the third port; and
      a valve element defining a first valve fluid path and a second valve fluid path,
      wherein the patient line is in fluid communication with the fourth port,
      wherein the first valve fluid path provides fluid communication between the first port and the second port in a delivery position of the valve housing relative to the valve element,
      wherein the second valve fluid path provides fluid communication between the third port and the fourth port in the delivery position,
      wherein the third port is isolated from the fourth port in a stop position of the valve housing relative to the valve element, and
      wherein the first valve fluid path provides fluid communication between the first port and the fifth port when in a fill position of the valve housing relative to the valve element.

8. The fluid delivery system of claim 7, further comprising: an actuator operably associated with the air detector and configured to transition the valve assembly to the stop position upon detection of air bubble by the air detector,
   wherein the air detector is upstream of or within the first port and configured to detect an air bubble flowing out of the at least one syringe.

9. The fluid delivery system of claim 7, wherein the fluid path length comprises tubing having a length greater than a distance that the air bubble can travel or expand during an actuation time of the valve assembly, and wherein the actuation time of the valve assembly is a time interval between a time at which the air bubble is detected by the air detector and a time at which the valve assembly reaches the stop position.

10. The fluid delivery system of claim 7, wherein the fluid path length comprises tubing have a length of between approximately 1000 millimeters and approximately 1400 millimeters.

11. The fluid delivery system of claim 7, wherein the first port, the second port, the third port, and the fourth port are arranged circumferentially about the valve housing and wherein the valve element is rotatable about a longitudinal axis of the valve housing between the delivery position and the stop position.

12. The fluid delivery system of, claim 7, wherein the first port is offset relative to the second port along a longitudinal axis of the valve housing.

13. The fluid delivery system of, claim 7, wherein the fluid path length comprises coiled tubing.

* * * * *

UNITED STATES PATENT AND TRADEMARK OFFICE
CERTIFICATE OF CORRECTION

| | |
|---|---|
| PATENT NO. | : 12,427,247 B2 |
| APPLICATION NO. | : 17/801975 |
| DATED | : September 30, 2025 |
| INVENTOR(S) | : Cowan et al. |

It is certified that error appears in the above-identified patent and that said Letters Patent is hereby corrected as shown below:

In the Specification

In Column 2, Line 20, delete "fluid path length fluid path length" and insert -- fluid path length --, therefor.
In Column 2, Line 32, delete "thee valve" and insert -- the valve --, therefor.
In Column 4, Lines 20-21, delete "including a including" and insert -- including --, therefor.
In Column 12, Line 7, delete "to such as" and insert -- such as --, therefor.
In Column 12, Line 17, delete "though," and insert -- through, --, therefor.
In Column 12, Line 46, delete "communication" and insert -- communication to --, therefor.
In Column 12, Line 48, delete "on" and insert -- one --, therefor.
In Column 14, Line 34, delete "is a" and insert -- if a --, therefor.
In Column 14, Line 62, delete "associated" and insert -- associated with --, therefor.
In Column 15, Line 6, delete "than an" and insert -- that an --, therefor.
In Column 16, Line 23, delete "arrange" and insert -- arranged --, therefor.
In Column 17, Line 6, delete "is fluid" and insert -- is in fluid --, therefor.
In Column 19, Line 52, delete "increase" and insert -- increased --, therefor.
In Column 20, Line 16, delete "tubing or" and insert -- tubing --, therefor.
In Column 20, Line 33, delete "high pressure a CV" and insert -- high pressure of CV --, therefor.
In Column 22, Line 31, delete "fluid path 160 path may" and insert -- fluid path 160 may --, therefor.
In Column 26, Line 52, delete "one in any" and insert -- in any one --, therefor.
In Column 27, Line 16, delete "bend" and insert -- bent --, therefor.
In Column 27, Line 59, delete "and/or or" and insert -- and/or --, therefor.

In the Claims

In Column 29, Line 18, in Claim 7, delete "assembly; and" and insert -- assembly; --, therefor.
In Column 29, Line 19, in Claim 7, delete "line," and insert -- line; and --, therefor.

Signed and Sealed this
Twenty-fifth Day of November, 2025

John A. Squires
*Director of the United States Patent and Trademark Office*

CERTIFICATE OF CORRECTION (continued)
U.S. Pat. No. 12,427,247 B2

In Column 30, Line 35, in Claim 12, delete "The fluid delivery system of, claim 7," and insert -- The fluid delivery system of claim 7, --, therefor.

In Column 30, Line 39, in Claim 13, delete "The fluid delivery system of, claim 7," and insert -- The fluid delivery system of claim 7, --, therefor.